United States Patent
Yin et al.

(10) Patent No.: US 11,566,040 B2
(45) Date of Patent: Jan. 31, 2023

(54) **SYNTHESIS OF O-ANTIGEN OLIGOSACCHARIDE COMPOUNDS OF *HELICOBACTER PYLORI* SEROTYPE O2**

(71) Applicant: Jiangnan University, Wuxi (CN)

(72) Inventors: Jian Yin, Wuxi (CN); Jing Hu, Wuxi (CN); Zhonghua Liu, Wuxi (CN); Chunjun Qin, Wuxi (CN)

(73) Assignee: Jiangnan University, Wuxi (CN)

( * ) Notice: Subject to any disclaimer, the term of this patent is extended or adjusted under 35 U.S.C. 154(b) by 74 days.

(21) Appl. No.: 16/918,104

(22) Filed: Jul. 1, 2020

(65) Prior Publication Data

US 2020/0331951 A1 Oct. 22, 2020

Related U.S. Application Data

(63) Continuation of application No. PCT/CN2019/091200, filed on Jun. 14, 2019.

(30) Foreign Application Priority Data

Jan. 28, 2019 (CN) .......................... 2019100779441

(51) Int. Cl.
| | |
|---|---|
| *A61K 31/702* | (2006.01) |
| *C07H 15/203* | (2006.01) |
| *C07H 1/00* | (2006.01) |
| *C07H 15/18* | (2006.01) |
| *A61K 45/06* | (2006.01) |

(52) U.S. Cl.
CPC ............. *C07H 15/203* (2013.01); *C07H 1/00* (2013.01); *C07H 15/18* (2013.01); *A61K 45/06* (2013.01)

(58) Field of Classification Search
CPC ........ C07H 15/203; C07H 1/00; C07H 15/18; A61K 45/06

USPC ........................................................ 514/25
See application file for complete search history.

(56) References Cited

FOREIGN PATENT DOCUMENTS

| CN | 108558961 A | 9/2018 |
|---|---|---|
| CN | 109776634 A | 5/2019 |

OTHER PUBLICATIONS

Baumann et al. (Eur. J. Org. Chem. 2018, 3803-3815).*
Boltje et al. (Nature Chemistry | vol. 1 | Nov. 2009, pp. 611-622).*
PCT/CN2019/091200 ISR dated Oct. 24, 2019.
Stacey Britton et. al., A novel Helicobacter pylori cell-surface polysaccharide, Carbohydrate Research 340 (2005) 1605-1611.

* cited by examiner

*Primary Examiner* — Shaojia A Jiang
*Assistant Examiner* — Michael C Henry
(74) *Attorney, Agent, or Firm* — IPro, PLLC

(57) ABSTRACT

Disclosed is synthesis of an O-Antigen oligosaccharide compound of *Helicobacter pylori* serotype O2, belonging to the field of organic synthesis. The disclosure obtains O-antigen disaccharide to tetracosasaccharide of *Helicobacter pylori* serotype $O_2$ by chemical synthesis. A chemical synthesis method which is quite conducive to production of a glucose-α-lglucosidic bond is developed in the disclosure by a protectant strategy, temperature effect, solvent effect, and additive effect. The method is applied in synthesis of an O-antigen oligosaccharide compound of *Helicobacter pylori* serotype O2 assembled with an amino linking arm. A saccharide conjugate can be prepared from the synthesized O-antigen oligosaccharide compound of *Helicobacter pylori* serotype O2 assembled with an amino linking arm together with a carrier protein for immunology researches, playing an important role in preventing and treating *Helicobacter pylori*.

5 Claims, 7 Drawing Sheets

SYNTHESIS OF O-ANTIGEN OLIGOSACCHARIDE COMPOUNDS OF HELICOBACTER PYLORI SEROTYPE O2

TECHNICAL FIELD

The disclosure herein relates to the field of synthesis of an O-antigen oligosaccharide compound of *Helicobacter pylori* serotype O2, belonging to the field of organic synthesis.

BACKGROUND

*Helicobacter pylori* is a microaerobic Gram-negative bacterium. About a half of the populations across the world have been infected with this pathogenic bacterium. Due to the low socioeconomic status and poor medical conditions, the proportion in developing countries is even up to 80%. It is reported that 47% and 66% of the populations in urban and rural areas of China are infected with *Helicobacter pylori*. Oral-oral transmission and fecal-oral transmission are the most major transmission modes of the pathogenic bacterium, and mother-to-child transmission is also one of transmission modes of the pathogenic bacterium.

Most *Helicobacter pylori* infection occurs in childhood. Once infected, the pathogenic bacterium may exist on the gastric mucosa for a lifetime. Although 70% of the infected are asymptomatic clinically, it is verified that this pathogenic bacterium is associated with a series of gastrointestinal diseases. 15%-20% of those long-term infected people will suffer from a series of gastrointestinal diseases including gastritis, gastric and duodenal ulcers, and the like. Besides, gastric cancer will be developed among 1%-2% of those long-term infected people. Gastric cancer has become a cancer with the fifth highest morbidity (about 952000 cases, accounting for 6.2% of cancer patients according to WHO data in 2012) and the third mortality (about 723000 cases accounting for 8.8% of cancer patients according to WHO data in 2012) across the globe. The International Agency for Research on Cancer (IACR) affiliated to WHO classified *Helicobacter pylori* as Class I cancerogen in 1994.

Currently, the major therapeutic method for gastrointestinal diseases associated with *Helicobacter pylori* infection is a combined therapeutic method using two antibiotics (metronidazole and clarithromycin) and a proton pump inhibitor, and is referred to as a triple therapy. This method has achieved some effects on treating *Helicobacter pylori*, but still has quite a few shortcomings. The main restrictions are manifested in: 1) antibiotics have a short metabolic period of time in gastrointestinal tracts; 2) antibiotics are not stable relatively in this special low pH environment of the stomach; 3) *Helicobacter pylori* generally lives at the gastric mucosa, while antibiotics have quite low concentrations at the gastric mucosa; and 4) more importantly, the therapeutic effect of antibiotics has a tendency of gradually weakening as drug-resistant bacteria come into being. Based on the defects above, it is reported that the one-year recurrence rate of *Helicobacter pylori* after treatment with the triple therapy reaches 15%-30%.

Accordingly, for overcoming this defect, researches concerning vaccines against this pathogenic bacterium have received more and more attention. For the past few years, researches on vaccines against the *Helicobacter pylori* focused on virulence factor antigens, such as urease B, cytotoxin-associated toxin (CagA), vacuolar toxin (VacA), flagellum, heat shock protein, adhesin, and neutrophil activating protein. In addition, a research on inactivated whole cells and lysate is also one of hot issues regarding vaccines.

At present, the researches on *Helicobacter pylori* lipopolysaccharide are mainly on extraction from inactivated bacteria. The deficiency of this method is that quite few products are obtained from extraction at a time. Besides, subjecting to the characteristics of bacterial gene expression and modification, the extracted lipopolysaccharide also has the characteristics including inconsistent structure, easy attachment of impurities with similar structures, and poor experimental repeatability, imposing some disturbances on the researches. We use a chemical synthesis method to produce O-antigen disaccharide, tetrasaccharide, and hexaose with the O-antigen oligosaccharide of *Helicobacter pylori* serotype O2 as a target compound, and through the design and construction of glycosyl building blocks as well as selection and optimization of glycosylation. Moreover, a reducing end of each of the synthesized disaccharide, tetrasaccharide, and hexaose are assembled with an amino linking arm, and can be connected with a carrier protein to form a glycoconjugate for conducting further immunology researches.

SUMMARY

The technical problem to be solved by the disclosure is to synthesize an O-antigen oligosaccharide fragment of *Helicobacter pylori* serotype O2. Constructing a 1,2-α-cis-glycosidic bond is the key step of synthesizing a target structure. In the disclosure, with diacetone glucose as the only starting material, protected disaccharide, tetrasaccharide, and hexaose connected with a protected holo-α-glycosidic bond are finally obtained through construction of glycosyl building blocks and optimization of the conditions for glycosylation, and finally deprotection is carried out to obtain the final target compound O-antigen disaccharide, tetrasaccharide, and hexaose of *Helicobacter pylori* serotype O2 assembled with amino linking arms. Meanwhile, a reducing end of each of the resulting disaccharide, tetrasaccharide, and hexaose synthesized with the method is assembled with an amino linking arm, and can be combined with a carrier protein for immunological researches.

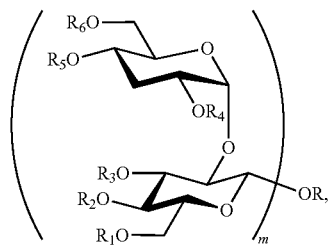

Formula I wherein m is the number of repeat units of a disaccharide fragment, and may be 2 to 12;

R is —(CH$_2$)$_n$—N—Y$_1$Y$_2$ or —(CH$_2$)$_n$—N—Y$_1$Y$_2$ (linker), n is 1 to 10, N is nitrogen, Y$_1$ is hydrogen or alkoxy such as benzyl (Bn), Y$_2$ is hydrogen (H) or alkoxycarbonyl such as benzyl methoxycarbonyl (Cbz); R$_1$, R$_2$, R$_3$, R$_4$, R$_5$, and R$_6$ each are hydrogen or an ether group such as benzyl (Bn).

The first object of the disclosure is to provide a method for preparing an O-antigen oligosaccharide compound of *Helicobacter pylori* serotype O2. The method constructs an O-antigen oligosaccharide compound of *Helicobacter pylori* serotype O2 by using saccharide building blocks A, B, and C, including constructing a 1,2-α-cis-glycosidic bond and a 1,3-α-cis-glycosidic bond between saccharide building blocks;

wherein the saccharide building blocks A, B, and C are compounds represented by structural formulae II and III, respectively:

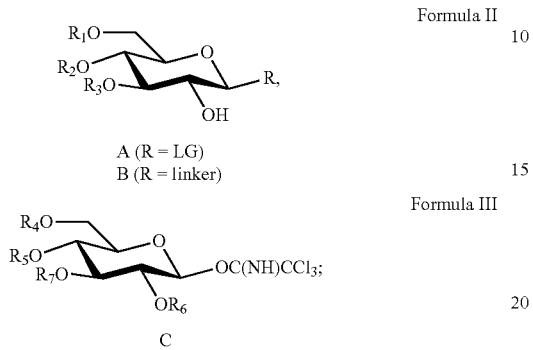

A (R = LG)
B (R = linker)

wherein LG is a leaving group for glycosylation, including trichloroacetylimino and p-methylphenylthio; a linker comprises $-(CH_2)_n-N-Y_1Y_2$ or $-(CH_2)_n-N-Y_1Y_2$ (linker), $Y_1$ is hydrogen (H) or alkoxy such as benzyl (Bn), and $V_2$ is hydrogen (H) or alkoxycarbonyl such as benzyl methoxycarbonyl (Cbz);

$R_1$, $R_2$, $R_3$, $R_4$, $R_5$, and $R_6$ each are hydrogen or an ether group; and $R_7$ is hydrogen or an acyl group.

In one embodiment of the disclosure, the construction of the 1,3-α-cis-glycosidic bond in the method is carried out in a mixed solvent of dichloromethane and ether.

In one embodiment of the disclosure, a volume ratio of dichloromethane to ether in the mixed solvent is 1:(2.5-5).

In one embodiment of the disclosure, the construction of the 1,3-α-cis-glycosidic bond in the method further requires introduction of an additive.

In one embodiment of the disclosure, the additive includes thiophene.

In one embodiment of the disclosure, a molar ratio of the additive to the saccharide building blocks is (80-120):1.

In one embodiment of the disclosure, the construction of the 1,2-α-cis-glycosidic bond in the method is carried out in a dichloromethane solvent.

In one embodiment of the disclosure, preferably, the method for constructing the 1,3-glucose-α-glycosidic bond includes that: a glycosyl donor and a glycosyl receptor are subjected to azeotropy in methylbenzene, dichloromethane and ether are added, the concentration of a reaction substrate is 0.01 to 0.1 M, a molecular sieve is used as a drying agent, 100-fold equivalents of thiophene (relative to the glycosyl donor) is added, stirring is carried out at the room temperature for 30 min followed by cooling to 0° C., and the reaction lasts for 12 h, and is terminated with pyridine.

In one embodiment of the disclosure, the method includes the following steps of:

(1) synthesizing glucose monosaccharide building blocks A, B, and C;

(2) synthesizing a disaccharide compound: constructing a 1,2-α-cis-glycosidic bond between saccharide building blocks; and (3) synthesizing tetrasaccharide compounds: constructing a 1,3-α-cis-glycosidic bond between the resulting disaccharide compounds in step (2).

In one embodiment of the disclosure, the method further includes that: with reference to step (3), polysaccharide compounds and a 1,3-α-cis-glycosidic bond between the polysaccharide compounds are constructed to prepare an O-antigen oligosaccharide compound of *Helicobacter pylori* serotype O2. The polysaccharide compound is a compound represented by formula IV:

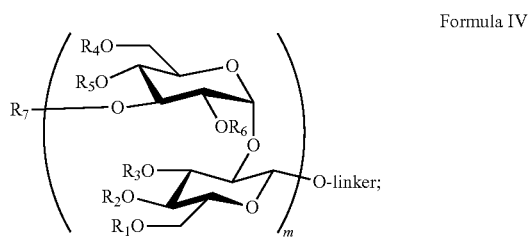

wherein m is the number of repeat units of a disaccharide fragment, and is 2 to 12;

a linker includes $-(CH_2)_n-N-Y_1Y_2$ or $-(CH_2)_n-N-Y_1Y_2$(linker), $V_1$ is hydrogen (H) or alkoxy such as benzyl (Bn), and $Y_2$ is hydrogen (H) or alkoxycarbonyl such as benzyl methoxycarbonyl (Cbz);

$R_1$, $R_2$, $R_3$, $R_4$, $R_5$, and $R_6$ each are hydrogen or an ether group; and $R_7$ is hydrogen or an acyl group.

In one embodiment of the disclosure, the method for synthesizing the monosaccharide building block A in step (1) includes that: 3-benzyl-diacetone-glucose is produced with diacetone glucose as a starting material in the presence of sodium hydride (NaH) and benzyl bromide (BnBr); afterwards, two propylene rings are hydrolyzed with an acid; naked hydroxyl groups of the resulting 3-benzyl compound produced are protected with acetyl groups; then, end group positions are protected with phenylthio in the presence of p-methylbenzenethiol and Lewis acid ($BF_3E_2tO$); next, the remaining acetyl groups at positions 2, 4, 6 are hydrolyzed in an alkaline environment; afterwards, the hydroxyl groups at positions 4, 6 are protected with benzylidene at the same time; and 2-OH is vacated to obtain the saccharide building block A.

In one embodiment of the disclosure, the method for synthesizing the monosaccharide building block A in step (1) specifically includes that: with the commercially available diacetone glucose as a starting material, protection is carried out at position 3 with allyl in the presence of sodium hydride (NaH) and allyl bromide (AllBr); afterwards, two propylidenes of the 3-allyl compound are removed by using allylalcohol (AllOH) and a hydrochloric acid, and the other position is also protected with allyl at the same time; then the remaining three hydroxyl groups of the glucose are protected with benzyl groups in the presence of sodium hydride (NaH) and benzyl bromide (BnBr); next, two allyl groups at positions 1, 3 of the glucose are deprotected in the presence of palladium chloride ($PdCl_2$) and methanol followed by protecting positions 1, 3 with acetyl groups in the presence of pyridine and acetic anhydride; finally, acetyl at position 1 of the glucose is selectively removed with hydrazine acetate; and the resulting 1-OH compound is made into a glycosyl donor, i.e. the saccharide building block A, with trichloroacetonitrile and DBU.

In one embodiment of the disclosure, the monosaccharide building block A is synthesized in an organic solvent including one or more of dichloromethane, ethyl acetate, methanol, N,N-dimethylformamide, tetrahydrofuran, pyridine, and chloroform.

In one embodiment of the disclosure, the concentration of a substrate is 0.02 to 0.5M in the synthesis reaction of the monosaccharide building block A.

In one embodiment of the disclosure, the acid is a hydrochloric acid, acetic acid or p-toluenesulfonic acid.

In one embodiment of the disclosure, the reaction temperature is −78° C. to a temperature for solvent reflux, and the reaction time is 1 to 48 h.

The structural formula of saccharide building block A is represented by formula II. Phenylthio is at the end group position, and is a leaving group.

In one embodiment of the disclosure, the method for synthesizing the monosaccharide building block B in step (1) includes that: 2-OH of the monosaccharide building block A above is protected with acetyl; the resulting 2-OAc compound reacts with a linking arm to obtain a glucose compound with a linking arm at an end group position; and finally, 2-OAc is removed in methanol and sodium methoxide to obtain the glucose building block B.

In one embodiment of the disclosure, the disaccharide compound in step (2) includes a disaccharide donor D and a disaccharide receptor E represented by formula V:

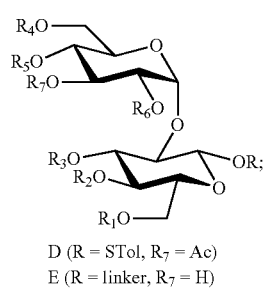

Formula V

D (R = STol, $R_7$ = Ac)
E (R = linker, $R_7$ = H)

wherein a linker includes —(CH$_2$)$_n$—N—Y$_1$Y$_2$ or —(CH$_2$)$_n$—N—Y$_1$Y$_2$(linker), Y$_1$ is hydrogen (H) or alkoxy such as benzyl (Bn), and Y$_2$ is hydrogen (H) or alkoxycarbonyl such as benzyl methoxycarbonyl (Cbz);

R$_1$, R$_2$, R$_3$, R$_4$, R$_5$, and R$_6$ each are hydrogen or an ether group; and R$_7$ is hydrogen or an acyl group.

In one embodiment of the disclosure, the step (2) includes: with saccharide building blocks A and C as materials and dichloromethane as a solvent, adding a drying agent, and performing reaction at −78° C. to obtain the disaccharide donor D; and synthesizing the disaccharide receptor E with saccharide building blocks B and C, performing glycosylation by a method that is the same as that for synthesizing the disaccharide donor D, after glycosylation is finished, removing 3'-OAc with a sodium methoxide solution after the product is purified to obtain the disaccharide receptor E.

The drying agent is one or more of 3 Å molecular sieve, 4 Å molecular sieve, 5 Å molecular sieve, anhydrous sodium sulfate, anhydrous magnesium sulfate, and anhydrous calcium sulfate.

A mass ratio of the drying agent to the reactant is 1.0 to 4.0.

In one embodiment of the disclosure, in the step (2), a TLC plate is used to monitor the reaction process in the reaction. Pyridine is used to terminate the reaction after the reaction is finished. The product is purified by a silicagel column.

In one embodiment of the disclosure, the step (3) includes: synthesizing a tetrasaccharide compound with the disaccharide donor D and the disaccharide receptor E.

In one embodiment of the disclosure, the tetrasaccharide compound includes a tetrasaccharide donor F and a tetrasaccharide receptor G represented by formula VI:

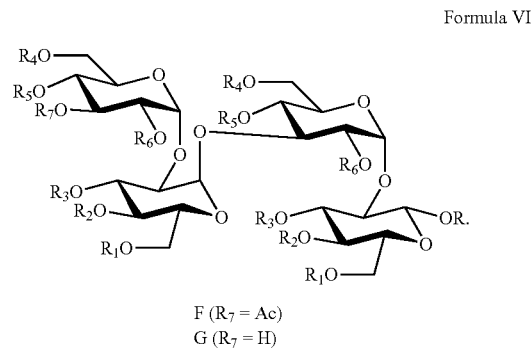

Formula VI

F ($R_7$ = Ac)
G ($R_7$ = H)

In one embodiment of the disclosure, the step (3) includes: adding an additive thiophene in a mixed solvent of DCM and Et$_2$O, with 4 Å molecular sieve as a drying agent, and performing reaction at 0° C. to a room temperature to obtain the tetrasaccharide F; and removing 3"-OAc from the tetrasaccharide E in a sodium methoxide solution to obtain the tetrasaccharide G.

In one embodiment of the disclosure, an accelerator may be further added when the tetrasaccharide F is prepared.

In one embodiment of the disclosure, the accelerator includes one or more of N-iodosuccinimide NIS, trimethylsilyl trifluoromethanesulfonate TMSOTf, trifluoromethanesulfonic acid TfOH, and silver trifluoromethanesulfonate AgOTf.

In one embodiment of the disclosure, a volume ratio of DCM to Et$_2$O in the mixed solvent is preferably 1:3.

In one embodiment of the disclosure, with reference to the method for constructing the tetrasaccharide, a series of oligosaccharide compounds of *Helicobacter pylori* serotype O2 such as octasaccharide, decasaccharide, and dodecaose may be further synthesized.

In one embodiment of the disclosure, an oligosaccharide chain may extend from a reducing end to a non-reducing end in a mode of binding to disaccharide, including two steps: 1) removing a lipid group at the non-reducing end from an oligosaccharide with a linking arm at the reducing end; and 2) performing glycosylation with a disaccharide donor 16.

In one embodiment of the disclosure, a hexaose compound is synthesized by constructing a 1,3-α-cis-glycosidic bond with disaccharide and tetrasaccharide. The hexaose compound includes a compound represented by formula VII:

Formula VII

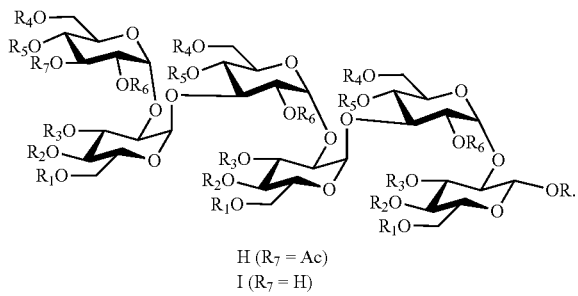

H (R₇ = Ac)
I (R₇ = H)

In one embodiment of the disclosure, the conditions for synthesizing a disaccharide compound are as follows: monosaccharide building blocks A and B (LG/linker) are used as substrates; dichloromethane is used as a reactive solvent; a drying agent is used; the reaction temperature is −78° C., and glycosylation is carried out under catalysis of Lewis acid. The reaction processes are protected by inert gases. After the reaction materials disappear, the reaction is quenched with pyridine or triethylamine. Filtering, washing, quenching, and drying are carried out. The product is purified with a silicagel column to obtain disaccharide I/II respectively.

In one embodiment of the disclosure, the method for assembling a tetrasaccharide is as follows: the tetrasaccharide is assembled with a disaccharide compound I as a donor and a disaccharide compound II as a receptor. The reaction conditions is using the disaccharide compounds I and II as substrates, and a mixed solvent of dichloromethane and ether as a reactive solvent, and adding thiophene at the same time. A drying agent is used, and the reaction temperature is the room temperature. The reaction is performed under the catalysis of Lewis acid. The reaction processes are protected by inert gases, after the reaction materials disappear, filtering, washing, quenching, and drying are carried out, and the product is purified with a silicagel column to obtain the tetrasaccharide.

In one embodiment of the disclosure, the conditions for assembling a hexaose are as follows: a non-reducing ester group is removed from a tetrasaccharide compound under alkaline conditions, and then the tetrasaccharide compound and a disaccharide compound I are used as substrates to assemble a hexaose compound. The reaction conditions are the same as that for assembling the tetrasaccharide compound.

In one embodiment of the disclosure, the method further includes deprotection.

In one embodiment of the disclosure, the deprotection is that all aromatic groups are removed by using Pd/C and under reaction in hydrogen for 24 h, and purification is carried out via a C18 reversed-phase column to obtain an O-antigen oligosaccharide compound of *Helicobacter pylori* serotype O2.

In one embodiment of the disclosure, the deprotection specifically includes:

1) removing acyl under alkaline conditions, wherein a solvent used is a mixed solvent consisting of one or more of methanol, tetrahydrofuran, and ethyl acetate; performing neutralization with H+ resin at the end of reaction to obtain a semi-deprotected saccharide compound, wherein the reaction temperature is the room temperature to 40° C. and the reaction time is 2 h to 2 d; and 2) fully deprotecting the semi-deprotected product with palladium/carbon and hydrogen, wherein a reactive solvent is one or more of tetrahydrofuran, dichloromethane, ethyl acetate, tertiary butanol, water, methanol, and acetic acid. The palladium carbon used is 10% palladium carbon, a mass ratio of the palladium carbon to the reactant is 0.1:1 to 0.5:1, a hydrogen pressure used by removing benzyl and benzylidene is 1 to 100 atm, the reaction temperature is the normal temperature and the reaction time is 2 to 48 h.

The second object of the disclosure is to provide an O-antigen oligosaccharide compound of *Helicobacter pylori* serotype O2 assembled with an amino linking arm. The structural formula thereof is represented by formula VIII. The compound is prepared with the method above:

Formula VIII

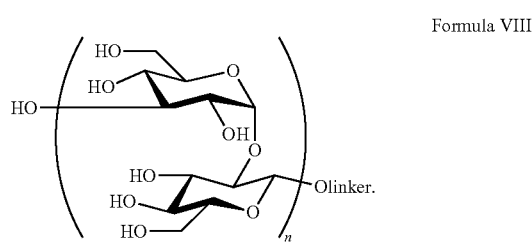

In one embodiment of the disclosure, the structure of the O-antigen oligosaccharide of *Helicobacter pylori* serotype O2 assembled with an amino linking arm is as follows:
α-D-Glc-(1-2)-α-D-Glc-(1-3)-α-D-Glc-(1-2)-α-D-Glc-(1-3)-α-D-Glc-(1-2)-α-D-Glc-linker.

The third object of the disclosure is to provide a method for preparing a glyco-protein conjugate. The O-antigen oligosaccharide compound of *Helicobacter pylori* serotype O2 assembled with an amino linking arm above is used in the method.

The fourth object of the disclosure is to apply the O-antigen oligosaccharide compound of *Helicobacter pylori* serotype O2 assembled with an amino linking arm above in developing or preparing a vaccine against *Helicobacter pylori* or a medicament for treating diseases caused by *Helicobacter pylori* infection.

The beneficial effects of the disclosure are as follows.

O-antigen disaccharide, tetrasaccharide, and hexaose of *Helicobacter pylori* serotype O2 are obtained by chemical synthesis in the disclosure. A method which is quite conducive to production of a glucose-α-glucosidic bond is found in the disclosure by a protectant strategy, temperature effect, solvent effect, and additive effect. Moreover, the method is applied in synthesis of O-antigen disaccharide, tetrasaccharide, and hexaose of *Helicobacter pylori* serotype O2. The reducing ends of the synthesized O-antigen disaccharide, tetrasaccharide, and hexaose of *Helicobacter pylori* serotype O2 are assembled with the amino linking arms and can be prepared into a saccharide conjugate with a carrier protein for immunology researches, playing an important role in preventing and treating *Helicobacter pylori*.

DETAILED DESCRIPTION

The embodiments of the disclosure are described in a detailed manner by combining examples. However, a person skilled in the art would understand that the following examples are only used for explaining the disclosure, and shall not be regarded as defining the scope of the disclosure. Those with no specific conditions indicated among the examples are implemented according to conventional conditions or manufacturers' suggestions. Any reagents or instruments with no manufacturer indicated are conventional products that can be purchased from the markets.

Example 1

Figure 1:
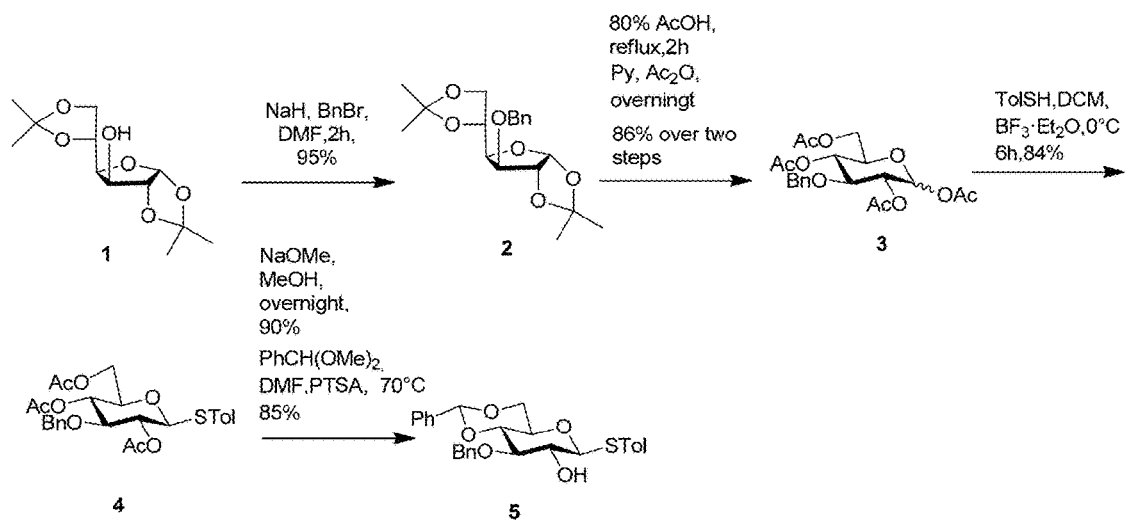
FIG. 1 shows synthesis of a monosaccharide building block 5 in Example 1.

Synthesis of a Saccharide Building Block 5 is as Shown in FIG. 1.

As shown in FIG. 1, commercially available diacetoneglucose 1 was used as a starting material, and reacted with benzyl bromide under the action of sodium cyanide to produce a 3-OBn glucose compound 2. After propylidene was removed in an 80% acetic acid solution, four new resulting hydroxyl groups were protected with acetyl groups in the presence of pyridine and acetic anhydride to obtain a compound 3. Thereafter, the compound 3 reacted with thiophenol in the presence of boron trifluorideether ($BF_3Et_2O$) to produce a 1-thioglycoside compound 4. Three acetyl groups of the compound 4 were removed with a methanol and sodium methoxide solution. Then hydroxyl groups at positions 4, 6 were protected with benzylidene in the presence of benzaldehyde dimethyl acetal and p-toluene naphthenic acid. A naked hydroxyl group at position 2 was reserved to produce a saccharide building block 5.

Specific test operation and steps are as follows.

Compound 2: diacetone glucose (50 g, 192 mmol) was dissolved in DMF (480 ml). Stirring was carried out at 0° C. for 20 min. Sodium cyanide (15.4 g, 284 mmol) was added slowly. Stirring was continued at 0° C. for 30 min, followed by adding benzyl bromide (34.2 ml, 288 mmol) into the reaction solution. The reaction was restored to the room temperature. Stirring was further performed for 3 h. The reaction solution was detected with TLC. After complete reaction of the raw materials, the reaction was quenched with ice water. Extraction was carried out with dichloromethane and a saturated saline solution. An organic phase was separated. and concentrated after drying with anhydrous sodium sulfate. Purification was carried out with a silicagel column (petroleum ether/ethyl acetate, 15:1) to obtain the compound 2 (67 g, 183 mmol, 95%). $^1$H NMR (400 MHz, Chloroform-d) δ 7.55-7.04 (m, 5H, Ar—H), 5.90 (d, J=3.7 Hz, 1H, H-1), 4.68 (d, J=11.8 Hz, 1H, Bn-H), 4.63 (d, J=11.8 Hz, 1H, Bn-H), 4.58 (d, J=3.7 Hz, 1H, H-2), 4.37 (dt, J=7.7, 6.1 Hz, 1H, H-5), 4.15 (dd, J=7.8, 3.2 Hz, 1H, H-6a), 4.11 (dd, J=9.1, 6.7 Hz, 1H, H-6b), 4.01-3.99 (m, 2H, H-3, H-4), 1.49 (s, 3H, Me-H), 1.43 (s, 3H, Me-H), 1.37 (s, 3H, Me-H), 1.31 (s, 3H, Me-H). $^{13}$C NMR (101 MHz, Chloroform-d) δ 137.65, 128.40 (2C), 127.84, 127.65 (2C), 111.79, 108.98, 105.30, 82.67, 81.72, 81.33, 72.54, 72.39, 67.40, 26.85, 26.79, 26.26, 25.45.

Compound 3: the compound 2 (67 g, 183 mmol) was dissolved in a 1 M hydrochloric acid (480 ml). Stirring was carried out at 80° C. for 2 h. The reaction was detected with TLC. After complete reaction of the raw materials and after the reaction solution was regulated to be neutral with a saturated sodium bicarbonate solution, the solvent was spun dry by rotary evaporation. The resulting product was subjected to azeotropy with methylbenzene three times, and vacuumized overnight by an oil pump.

The new resulting compound in the last step was dissolved in acetic anhydride (360 ml). Meanwhile, anhydrous sodium acetate (18.9 g) was added. The reaction solution was stirred at 80° C. for 4 h. After complete reaction of the raw materials was detected with TLC, the reaction solution was poured into ice water. Afterwards, extraction was carried out with ethyl acetate and saturated sodium bicarbonate. An organic phase was separated and concentrated after drying with anhydrous sodium sulfate. The concentrated solution was purified with a silicagel column (petroleum ether/ethyl acetate, 4:1) to obtain the compound 3 (69 g, 157 mmol, 86%). —Configuration: $^1$H NMR (400 MHz, Chloroform-d) δ 7.36-7.19 (m, 5H, Ar—H), 6.31 (d, J=3.6 Hz, 1H, 1-H), 5.16 (t, J=9.8 Hz, 1H, 4-H), 5.05 (dd, J=10.0, 3.7 Hz, 1H, 2-H), 4.71 (d, J=11.8 Hz, 1H, Bn-H), 4.63 (d, J=11.8 Hz, 1H, Bn-H), 4.24-4.16 (m, 1H, 6a-H), 4.09-3.92 (m, 3H, 3-H, 5-H, 6b-H), 2.16 (s, 3H, Me-H), 2.07 (s, 3H, Me-H), 1.99 (s, 3H, Me-H), 1.97 (s, 3H, Me-H). $^{13}$C NMR (101 MHz, Chloroform-d) δ 170.58 (d, J=2.1 Hz), 169.56, 169.25, 168.73, 137.94, 128.39 (2C), 127.78, 127.48 (2C), 89.41, 76.97, 74.81, 71.54, 70.24, 69.14, 61.82, 20.79 (2C), 20.63, 20.50. —Configuration: $^1$H NMR (400 MHz, Chloroform-d) δ 7.33-7.13 (m, 5H, Ar—H), 5.63 (d, J=8.2 Hz, 1H, 1-H), 5.12 (td, J=9.2, 4.2 Hz, 2H, 2-H, 4-H), 4.59 (s, 2H, 2Bn-H), 4.19 (dd, J=12.5, 5.0 Hz, 1H, 6a-H), 4.05 (dd, J=12.4, 2.3 Hz, 1H, 6b-H), 3.76-3.66 (m, 2H, 3-H, 5-H), 2.05 (s, 3H, Me), 2.02 (s, 3H, Me), 1.94 (s, 6H, 2Me). $^{13}$C NMR (101 MHz, Chloroform-d) δ 170.55, 169.26, 169.08, 169.02, 137.59, 128.43, 127.89, 127.76, 91.92, 79.90, 74.19, 72.89, 71.54, 69.09, 61.78, 20.75, 20.62.

Compound 4: the compound 3 (42 g, 96 mmol) was dissolved in anhydrous DCM (240 ml). P-methylthiophenol (17.9 g, 144 mmol) and an appropriate amount of fresh and activated molecular sieves were added and stirred at the room temperature for 30 min. Then, the temperature was reduced to 0° C. After continued stirring for 20 min, boron trifluoride diethyl etherate (60 ml) was added slowly. The reaction solution was stirred at the room temperature for 24 h. The reaction process was monitored with TLC. After complete reaction of the raw materials, the reaction solution was extracted with dichloromethane and a saturated sodium bicarbonate solution. An organic phase was separated and concentrated after drying with anhydrous sodium sulfate. The concentrated solution was purified with a silicagel column (petroleum ether/ethyl acetate, 4:1) to obtain the compound 4 (40.5 g, 81 mmol). 41 NMR (400 MHz, Chloroform-d) δ 7.45-6.91 (m, 9H, Ar—H), 5.05 (t, J=9.7 Hz, 1H, 4-H), 5.02 (t, J=9.5 Hz, 1H, 2-H), 4.64-4.51 (m, 3H, 1-H, 2Bn-H), 4.16 (t, J=3.4 Hz, 2H, 6ab-H), 3.71 (t, J=9.2 Hz, 1H, 3-H), 3.60 (ddd, J=9.9, 5.0, 3.1 Hz, 1H, 5-H), 2.33 (s, 1H, Me-H), 2.07 (s, 3H, Me-H), 2.04 (s, 3H, Me-H), 1.95 (s, 3H, Me-H). $^{13}$C NMR (101 MHz, Chloroform-d) δ 170.59, 169.32, 169.17, 138.38, 137.73, 133.26, 129.60, 128.44, 127.85, 127.76, 86.41, 81.59, 77.46, 77.14, 76.82, 76.06, 74.26, 71.40 (d, J=3.1 Hz), 69.71, 62.56, 21.14, 20.96, 20.75, 20.72.

Compound 5: the compound 4 (27 g, 54 mmol) was dissolved in methanol (150 ml). 5 M sodium methoxide (22 ml) was added under the room temperature. The reaction solution was further stirred at the room temperature for 2 h. The reaction was monitored with TLC. After complete reaction of the raw materials, the reaction solution was neutralized to be neutral with the Amberlite IR120 W resin. The resin was filtered out. The filtrate was spun dry to obtain a new compound (about 20 g) and vacuumized overnight by an oil pump.

The new compound (about 20 g, 53 mmol) was dissolved in anhydrous DMF. Benzaldehyde dimethyl acetal (8.3 ml) and p-methylbenzene sulfonic acid (1.0 g) were added successively. The reaction solution was stirred at 70° C. for 6 h. The reaction was monitored with TLC. After complete reaction of the raw materials, the reaction solution was neutralized with triethylamine. The reaction solution after being concentrated was extracted with dichloromethane and a saturated saline solution. An organic phase was separated and concentrated after drying with anhydrous sodium sulfate. The concentrated solution was purified with a silicagel column to obtain the compound 5 (19.1 g, 41 mmol). $^1$H NMR (400 MHz, Chloroform-d) δ 7.68-7.21 (m, 13H, Ar—H), 7.13 (d, J=7.9 Hz, 2H, Ar—H), 5.56 (s, 1H, PhCH—H), 4.94 (d, J=11.5 Hz, 1H, Bn-H), 4.78 (d, J=11.5 Hz, 1H, Bn-H), 4.56 (d, J=9.7 Hz, 1H, 1-H), 4.38 (dd, J=10.5, 4.9 Hz, 1H, 6a-H), 3.78 (t, J=10.3 Hz, 1H, 6b-H), 3.72-3.65 (m, 1H, 3-H), 3.63 (t, J=9.0 Hz, 1H, 4-H), 3.47 (td, J=9.3, 9.0, 5.8 Hz, 2H, 2-H, 5-H), 2.56-2.49 (m, 1H, 2OH—H), 2.34 (s, 3H, Me). $^{13}$C NMR (101 MHz, Chloroform-d) δ 138.75, 138.20, 137.20, 133.83, 129.81, 129.00, 128.45, 128.25, 128.11, 127.86, 127.20, 125.99, 101.24, 88.58, 81.61, 81.13, 74.81, 72.13, 70.73, 68.64, 21.17.

Example 2

Synthesis of Saccharide Building Block 8

Figure 2:
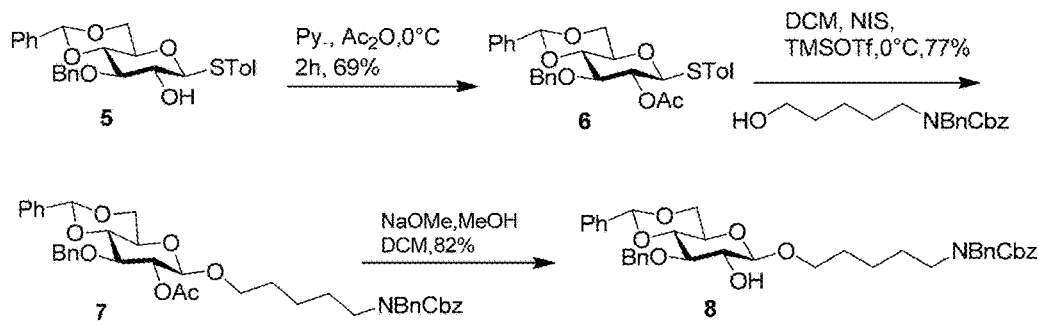
FIG. 2 shows synthesis of a monosaccharide building block 8 in Example 2.

Synthesis of a Saccharide Building Block 8 is as Shown in FIG. 2.

As shown in FIG. 2, a compound 8 is an analogue of the compound 5 with a reducing end assembled with an amino linking arm. Based on the compound 5, 2-OH was protected with acetyl first to obtain the compound 6. Then the p-methylphenylthio as a leaving group reacted with a five-carbon amino linking arm with NIS and TMSOTf as accelerators to obtain compound 7. Finally, 2-OAc of the compound 7 was removed with methanol and sodium methoxide to obtain the saccharide building block 8.

Specific test operation and steps are as follows.

Compound 6: the compound 5 (9.7 g, 21 mmol) was dissolved in dry pyridine (60 ml). Acetic anhydride (40 ml) was added slowly in an ice bath. The reaction solution was stirred at the room temperature for 6 h. After complete reaction of the raw materials was detected with TLC, the reaction solution was diluted with dichloromethane. Washing was carried out with a 1 M hydrochloric acid. Extraction was carried out with a saturated sodium bicarbonate solution and dichloromethane. An organic phase was separated and concentrated after drying with anhydrous sodium sulfate. The concentrated solution was purified with a silicagel column (petroleum ether/ethyl acetate, 7:1) to obtain the compound 6 (7.3 g, 14.4 mmol). $^1$H NMR (400 MHz, Chloroform-d) δ 7.54-7.19 (m, 12H, Ar—H), 7.11 (d, J=7.9 Hz, 2H, Ar—H) 5.56 (s, 1H, PhCH—H), 4.99 (dd, J=10.0, 8.6 Hz, 1H, 2-H), 4.85 (d, J=12.0 Hz, 1H, Bn-H), 4.68-4.60 (m, 2H, 1-H, Bn-H), 4.37 (dd, J=10.5, 5.0 Hz, 1H, 6a-H), 3.79 (t, J=10.3 Hz, 1H, 6b-H), 3.75-3.69 (m, 2H, 3-H, 4-H), 3.47 (dq, J=7.9, 5.0 Hz, 1H, 5-H), 2.33 (s, 3H, Me), 2.03 (s, 3H, Me). $^{13}$C NMR (101 MHz, Chloroform-d) δ 169.22, 138.26, 137.12, 133.39 (2C), 129.65 (2C), 128.99, 128.29 (2C), 128.24 (2C), 128.21, 127.87 (2C), 127.66, 125.96 (2C), 101.19, 86.96, 81.30, 79.77, 74.31, 71.35, 70.46, 68.53, 21.13, 20.95.

Compound 7: the compound 6 (7.3 g, 14.4 mmol) and nitrogen-benzyl-nitrogen-benzyl formate-pentanol (8.62 g, 28.8 mmol) were dissolved in anhydrous DCM (100 ml). An appropriate amount of fresh and inactivated molecular sieves was added. Stirring was carried out at the room temperature for 30 min. Thereafter; the mixture was transferred to an ice bath. NIS (5.6 g, 17.3 mmol) and TMSOTf (0.3 ml, 1.7 mmol) were added into the reaction solution at a time after 30 min. Reaction was continued in the ice bath for 10 h. The reaction process was monitored with TLC. After complete reaction of the raw materials, the reaction solution was extracted with 10% sodium thiosulfate, a saturated sodium bicarbonate solution, and dichloromethane successively. An organic phase was separated and concentrated after drying with anhydrous sodium sulfate. The concentrated solution was purified with a silicagel column (petroleum ether/ethyl acetate, 3:1) to obtain the compound 7 (7.5 g, 11.1 mmol).

Compound 8: the compound 7 (7.0 g, 10.3 mmol) was dissolved in methanol (50 ml). Sodium methoxide (110 mg) was added at the room temperature. The reaction solution was stirred at the room temperature for 8 h. The reaction was monitored with TLC. After complete reaction of the raw materials, the reaction solution was neutralized to be neutral with Amberlite IR120 H$^+$ resin. The resin was filtered out. Purification was carried out with a silicagel column (petroleum ether/ethyl acetate, 3:1) after concentration to obtain the compound 8 (4.6 g, 8.45 mmol).

Example 3

Synthesis of Saccharide Building Block 15

Figure 3:
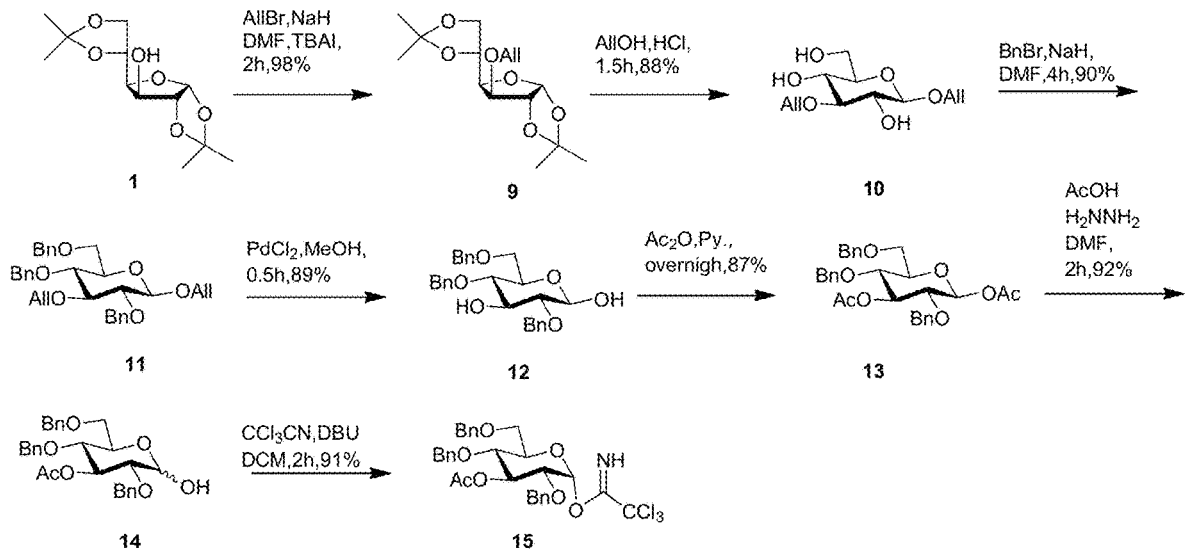
FIG. 3 shows synthesis of a monosaccharide building block 15 in Example 3.

As shown in FIG. 3, diacetone glucose 1 as a starting material reacted with allyl bromide in the presence of NaH to obtain 3-allyl compound 9. The compound 9 subjected to a ring-opening reaction in allyl alcohol added with a hydrochloric acid to obtain a 1,3-diallyl compound 10. The remaining three naked hydroxyl groups of glucose were protected with benzyl groups to obtain a compound 11. Allyl groups at positions 1, 3 of the compound 11 were removed specifically with palladium chloride in dry methanol to obtain a 1-OH compound 12. Two resulting hydroxyl groups in the previous step were protected with acetyl groups to obtain a compound 13. A 1-OAc group was selectively removed in the presence of hydrazine acetate to obtain a 1-OH compound 14. Finally, the compound 14 reacted with trichloroacetonitrile and DBU to obtain a trichloroacetimidate glycosyl building block 15.

Specific test operation and steps are as follows.

Compound 9: the commercially available diacetone glucose 1 (50 g, 191 mmol) was dissolved in anhydrous DMF (380 ml). Stirring was carried out in an ice bath for 30 min. Afterwards, sodium hydride (23 g) and allyl bromide (34 ml) were added in batches. Stirring was carried out for 2 h in the ice bath in the reaction. The reaction was monitored with TLC. After complete reaction of the raw materials, the reaction was quenched with ice water. The reaction solution was extracted with dichloromethane and a saturated saline solution and concentrated after drying with anhydrous sodium sulfate. The concentrated solution was purified with a silicagel column (petroleum ether/ethyl acetate, 20:1) to obtain the compound 9 (57.1 g, 190 mmol). 1H NMR (400 MHz, CDCl3): δ=5.95-5.77 (m, 2H, 1-H, Ally-H), 5.31 (dd, J=17.2, 1.7 Hz, 1H, Ally-H), 5.20 (dt, J=10.4, 1.5 Hz, 1H, Ally-H), 4.54 (d, J=3.7 Hz, 1H, 2-H), 4.31 (dt, J=7.7, 6.0 Hz, 1H, 5-H), 4.34-4.07 (m, 4H, 4-H, 6a-H, 2Ally-H), 4.00 (dd, J=8.6, 5.8 Hz, 1H, 6b-H), 3.94 (d, J=3.0 Hz, 1H, 3-H), 1.50 (s, 3H, Me), 1.43 (s, 3H, Me), 1.35 (s, 3H, Me), 1.31 (s, 3H, Me). $^{13}$C NMR (101 MHz, Chloroform-d) δ 134.28, 117.41, 111.88, 109.07, 105.36, 82.91, 81.53, 81.30, 72.62, 71.47, 67.41, 26.96, 26.93, 26.37, 25.54.

Compound 10: the compound 9 (52.8 g, 176 mmol) was dissolved in allyl alcohol (350 ml). A concentrated hydrochloric acid (10.5 ml) was added. The reaction solution was stirred at 80° C. for 2 h. The reaction was monitored with TLC. After complete reaction of the raw materials, the reaction solution was neutralized to be neutral with a saturated sodium bicarbonate solution. The reaction solution was concentrated, and purified with a silicagel column (dichloromethane/methyl alcohol, 25:1) to obtain the compound 10 (40.3 g, 155 mmol). $^1$H NMR (400 MHz, Chloroform-d) δ 6.01-5.74 (m, 2H, 2Ally-H), 5.24 (dt, J=17.3, 1.7 Hz, 2H, 2Ally-H), 5.15 (ddt, J=13.5, 10.4, 1.4 Hz, 2H, 2Ally-H), 4.83 (d, J=3.7 Hz, 1H, H-1), 4.38 (ddt, J=12.7, 5.7, 1.5 Hz, 1H, Ally-H), 4.22 (ddt, J=12.7, 6.0, 1.4 Hz, 1H, Ally-H), 4.15 (ddt, J=12.8, 5.3, 1.5 Hz, 1H, Ally-H), 3.97 (ddt, J=12.8, 6.3, 1.4 Hz, 1H, Ally-H). 3.75 (d, J=3.6 Hz, 2H, H-6ab), 3.59 (dt, J=9.2, 3.6 Hz, 1H, H-5), 3.53 (dd, J=9.1, 3.8 Hz, 1H, H-2), 3.51-3.42 (m, 2H, H-3, H-4). $^{13}$C NMR (101 MHz, Chloroform-d) δ 135.13, 133.49, 118.12, 117.33, 97.73, 82.36, 73.93, 72.52, 71.38, 69.84, 68.60, 62.04.

Compound 11: the compound 10 (38 g, 146 mmol) was dissolved in anhydrous DMF (365 ml). Stirring was carried out in an ice bath for 30 min. Sodium hydride (35 g) was added slowly in batches. Stirring was continued in the ice bath for 30 min. Benzyl bromide was added (61 ml). The reaction solution was further stirred for 5 h. The reaction was monitored with TLC. After complete reaction of the raw materials, the reaction was quenched with ice water. Extraction was carried out with a saturated saline solution and dichloromethane. An organic phase was separated and concentrated after drying with anhydrous sodium sulfate. The concentrated solution was purified with a silicagel column to obtain the compound 11 (67.8 g, 127.7 mmol). $^1$H NMR (400 MHz, Chloroform-d) δ 7.37 (ddt, J=21.5, 14.3, 6.6 Hz, 13H, Ar—H), 7.24 (d, J=7.1 Hz, 2H, Ar—H), 6.01 (dddt, J=34.9, 17.4, 11.7, 5.6 Hz, 1H, Ally-H), 5.35 (dt, J=16.1, 7.7 Hz, 1H, Ally-H), 5.23 (t, J=10.2 Hz, 1H, Ally-H), 4.87 (td, J=14.4, 12.4, 6.9 Hz, 2H, 1-H, Bn-H), 4.79 (d, J=6.0 Hz, 1H, Bn-H), 4.73-4.56 (m, 2H, 2Bn-H), 4.50 (t, J=11.7 Hz, 3H, Ally-H, 2Bn-H), 4.35 (td, J=15.1, 13.9, 5.8 Hz, 0H) 4.19 (dd, J=13.2, 5.6 Hz, Ally-H), 4.05 (dd, J=12.9, 6.8 Hz, Ally-H), 3.91 (q, J=7.8, 6.1 Hz, 1H, 3-H), 3.85-3.71 (m, 2H, 5-H, 6a-H), 3.65 (dt, J=14.7, 7.7 Hz, 2H, 4-H, 6b-H), 3.60-3.51 (m, 1H, 2-H). $^{13}$C NMR (101 MHz, CDCl$_3$) δ 138.54, 138.35, 138.24, 137.99, 135.40, 135.21, 134.12, 133.81, 128.43, 128.39, 128.37, 128.25, 128.09, 128.05, 128.03, 127.95, 127.93, 127.83, 127.80, 127.72, 127.62, 118.15, 117.20, 116.74, 116.54, 102.69, 95.82, 84.40, 82.19, 81.81, 79.65, 77.83, 77.68, 77.42, 77.33, 77.09, 77.01, 76.78, 76.70, 75.12, 75.05, 74.93, 74.85, 74.52, 74.42, 73.50, 73.22, 70.32, 70.20, 69.01, 68.48, 68.19.

Compound 12: the compound 11 (10.2 g, 19.3 mmol) was dissolved in absolute methanol (644 ml). Palladium chloride (684.5 mg) was added. The reaction solution was stirred at 40° C. for 20 min. The reaction was monitored with TLC. After complete reaction of the raw materials, the reaction solution was extracted with saturated sodium bicarbonate and dichloromethane. An organic phase was separated and concentrated after drying with anhydrous sodium sulfate. The concentrated solution was purified with a silicagel column (petroleum ether/ethyl acetate, 3:1) to obtain the compound 12 (6.5 g, 14.4 mmol). $^1$H NMR (400 MHz, Chloroform-d) δ 7.31-7.15 (m, 15H, Ar—H), 5.18 (d, J=3.5 Hz, 1H, 1-H), 4.92 (d, J=11.5 Hz, 1H, Bn-H), 4.77 (d, J=11.3 Hz, 1H, Bn-H), 4.65 (d, J=11.8 Hz, 1H, Bn-H), 4.59 (d, J=11.8 Hz, 1H, Bn-H), 4.54 (d, J=12.2 Hz, 1H, Bn-H), 4.43 (d, J=12.2 Hz, 1H, Bn-H), 4.04 (t, J=9.2 Hz, 1H, 3-H), 3.96 (ddd, J=10.1, 3.9, 2.5 Hz, 1H, 5-H), 3.66-3.58 (m, 2H, 6ab-H), 3.46 (dd, J=10.0, 8.9 Hz, 1H, 4-H), 3.36 (dd, J=9.5, 3.5 Hz, 1H, 2-H) 2.91 (s, 2H, OH—H). $^{13}$C NMR (101 MHz, CDCl3) δ 138.36, 137.80, 137.74, 128.62, 128.58, 128.44, 128.42, 128.20, 128.13, 128.10, 128.05, 128.00, 127.95, 127.91, 127.81, 127.78, 127.76, 97.11, 90.71, 82.19, 79.54, 77.65, 77.45, 77.41, 77.29, 77.09, 76.77, 76.56, 74.60, 74.52, 74.29, 73.50, 73.27, 72.83, 69.78, 68.72.

Compound 13: the compound 12 (6.1 g, 14 mmol) was dissolved in pyridine (40 ml). Stirring was carried out in an ice bath for 30 min. Acetic anhydride (30 ml) was added slowly.

The reaction solution was stirred overnight in the ice bath. The reaction process was monitored with TLC. After complete reaction of the raw materials, the reaction was quenched with a 1 M hydrochloric acid solution. The reaction solution was extracted with a saturated sodium bicarbonate solution and ethyl acetate. An organic phase was separated and concentrated after drying with anhydrous sodium sulfate. The concentrated solution was purified with a silicagel column (petroleum ether/ethyl acetate, 6:1) to obtain the compound 13 (6.77 g, 12.66 mmol). $^1$H NMR (400 MHz, Chloroform-d) δ 7.52-7.15 (m, 13H, Ar—H), 7.12 (dd, J=7.6, 1.9 Hz, 2H, Ar—H), 5.63 (d, J=8.1 Hz, 1H, H-1), 5.26 (t, J=9.4 Hz, 1H, H-3), 4.69 (d, J=12.0 Hz, 1H, Bn-H), 4.65 (d, J=12.0 Hz, 1H, Bn-H), 4.58 (d, J=12.0 Hz, 1H, Bn-H), 4.47 (t, J=6.0 Hz, 3H, Bn-H), 3.80-3.67 (m, 3H, H-4, H-6a, H-6b), 3.60 (dt, J=9.9, 2.5 Hz, 1H, H-5), 3.51 (dd, J=9.5, 8.1 Hz, 1H, H-2), 2.07 (s, 3H, Me), 1.84 (s, 3H, Me). $^{13}$C NMR (101 MHz, Chloroform-d) δ 169.80, 168.98, 137.88, 137.79, 128.43, 128.11, 127.88, 127.85, 127.83, 94.07, 78.45, 75.61, 75.53, 75.34, 74.38, 74.31, 73.64, 67.85, 21.07, 20.96.

Compound 14: the compound 13 (1.6 g, 3.0 mmol) was dissolved in anhydrous DMF (30 ml). Hydrazine acetate (305 mg) was added. The reaction solution was stirred at 40° C. for 2 h. The reaction was monitored with TLC. The reaction solution was concentrated after the complete reaction of the raw materials. Extraction was carried out with a saturated saline solution and DCM. An organic phase was separated and concentrated was carried out after drying with anhydrous sodium sulfate. The concentrated solution was purified with a silicagel column (petroleum ether/ethyl acetate, 2:1) to obtain the compound 14 (1.36 g, 2.76 mmol). $^1$H NMR (400 MHz, Chloroform-d) δ 7.37-7.21 (m, 13H, Ar—H), 7.13 (d, J=7.2 Hz, 2H, Ar—H), 5.50 (t, J=9.6 Hz, 1H, 3-H), 5.27 (d, J=3.6 Hz, 1H, 1-H), 4.67-4.37 (m, 6H, Bn-H), 4.07 (d, J=10.0 Hz, 1H, 6a-H), 3.78 (s, 1H, 1-OH), 3.73-3.58 (m, 3H, 4-H, 5-H, 6b-H), 3.48 (dd, J=9.8, 3.4 Hz, 1H, 2-H), 1.91 (s, 3H, Me). $^{13}$C NMR (101 MHz, CDCl$_3$) δ 170.14, 137.96, 137.77, 137.64, 128.53, 128.46, 128.43, 128.34, 128.13, 128.12, 128.03, 128.00, 127.95, 127.90, 127.86, 127.78, 90.86, 77.58, 77.50, 77.18, 76.86, 76.10, 74.36, 74.28, 73.90, 73.58, 73.55, 73.45, 72.56, 69.91, 68.37, 21.12.

Compound 15: the compound 14 (300 mg, 0.61 mmol) was dissolved in anhydrous DMF (6 ml). Trichloroacetonitrile (0.6 ml) and DBU (91 μL) were added in an ice bath. The reaction solution was stirred in the ice bath for 2 h. The reaction was monitored with TLC. After the complete reaction of the raw materials, the reaction solution was extracted with a saturated saline solution and dichloromethane. An organic phase was separated and concentrated after drying with anhydrous sodium sulfate. The concentrated solution was purified with a silicagel column to obtain the compound 15 (357 mg, 0.56 mmol). $^1$H NMR (400 MHz, Chloroform-d) δ 8.59 (s, 1H, NH—H), 7.28 (dt, J=19.8, 5.5 Hz, 13H, Ar—H), 7.19-7.14 (m, 2H, Ar—H), 6.54 (d, 1=3.5 Hz, 1H, H-1), 5.59 (t, J=9.7 Hz, 1H, H-3), 4.65 (d, J=12.4 Hz, 1H, Bn-H), 4.60 (d, J=11.9 Hz, 1H, Bn-H), 4.55-4.48 (m, 3H, Bn-H), 4.46 (d, J=11.8 Hz, 1H, Bn-H), 4.04 (dt, J=10.1, 2.5 Hz, 1H, H-6a), 3.84-3.73 (m, 2H, H-6b, H-4), 3.67 (dd, J=10.0, 3.6 Hz, 2H, H-2, H-5), 1.91 (s, 3H, Me). $^{13}$C NMR (101 MHz, Chloroform-d) δ 169.87, 161.34, 137.82, 137.77, 137.74, 93.96, 91.20, 76.51, 75.48, 74.66, 73.67, 73.19, 72.99, 72.53, 67.90, 21.12.

Example 4

Synthesis of Disaccharide Compounds 16 and 18

Figure 4:
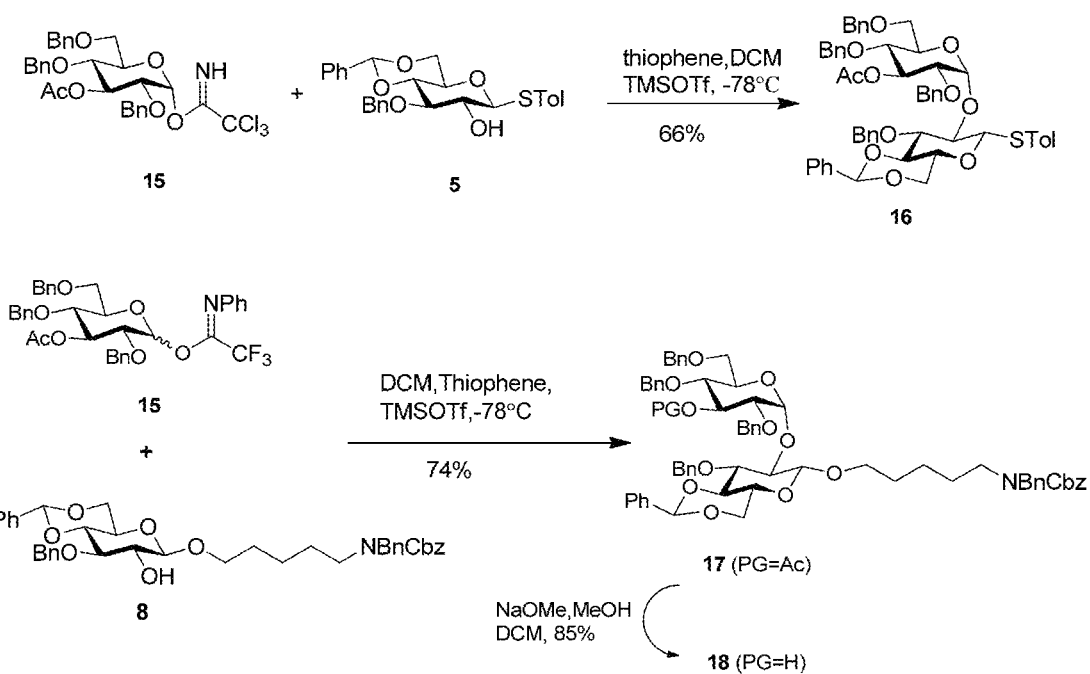
FIG. 4 shows synthesis of disaccharide compounds 16 and 18 in Example 4.

As shown in FIG. 4, a disaccharide compound 16 is synthesized by a monosaccharide donor 15 and a monosaccharide receptor 5 with TMSOTf as an accelerator. A disaccharide compound 17 was synthesized by a monosaccharide donor 15 and a monosaccharide receptor 8 with a similar method. Thereafter, 3'-OAc of the compound 17 is removed in the presence of methanol and sodium methoxide to obtain a disaccharide compound 18.

Compound 16: a glycosyl donor 15 (3.1 g, 4.8 mmol) was mixed with a glycosyl donor (2.8 g, 6.1 mmol), and subjected to azeotropy with methylbenzene 3 times under the protection of nitrogen. Vacuumization was performed overnight by an oil pump.

Dichloromethane (100 ml) and an appropriate amount of molecular sieves were added. Stirring was carried out at the room temperature for 30 min followed by cooling to −78° C. Stirring was further performed for 30 min. An accelerator TMSOTf (100 μL) was added. Stirring was carried out at low temperature for 5 h in the reaction. The reaction process was monitored with TLC. The reaction was quenched with triethylamine after complete consumption of the glycosyl donor in the reaction. The reaction solution was extracted with dichloromethane and a saturated sodium bicarbonate solution. An organic phase was separated and concentrated after drying with anhydrous sodium sulfate. The concentrated solution was purified with a silicagel column (petroleum ether/ethyl acetate, 10:1) to obtain the compound 16 (2.9 g, 3.2 mmol). $^1$H NMR (400 MHz, Chloroform-d) δ 7.52-7.45 (m, 2H, Ar—H), 7.41-7.23 (m, 21H, Ar—H), 7.14 (td, J=7.5, 1.6 Hz, 3H, Ar—H), 7.07 (d, J=7.9 Hz, 2H, Ar—H), 7.02 (t, J=7.6 Hz, 2H, Ar—H), 5.99 (d, J=3.7 Hz, 1H, 1'-H), 5.60 (s, 1H, PhCH), 5.55 (t, J=9.7 Hz, 1H, 3'-H), 4.99 (d, J=10.1 Hz, 1H, Bn-H), 4.90 (d, J=8.9 Hz, 1H, 1-H), 4.85 (d, J=12.2 Hz, 1H, Bn-H), 4.64 (d, J=10.2 Hz, 1H, Bn-H), 4.61-4.51 (m, 2H, 2Bn-H), 4.47 (d, J=11.2 Hz, 1H, Bn-H), 4.41-4.35 (m, 1H, 6A-H), 4.34 (d, J=11.0 Hz, 1H, Bn-H), 4.26 (dd, J=11.1, 5.3 Hz, 2H, 5'-H, Bn-H), 3.93-3.83 (m, 2H, 2-H, 3-H), 3.80 (d, J=10.3 Hz, 1H, 6A-H), 3.74 (dd, J=12.3, 3.3 Hz, 1H, 4-H), 3.71-3.66 (m, 1H, 4'-H), 3.56 (dd, J=10.3, 3.6 Hz, 1H, 2'-H), 3.51 (dd, J=9.6, 5.0 Hz, 1H, 5-H), 3.17-3.06 (m, 2H, 6'-H), 2.35 (s, 3H, Me), 1.96 (s, 3H, Me)$^{13}$C NMR (101 MHz, CDCl$_3$) δ 192.42, 170.09, 163.32, 138.36, 138.26, 138.17, 138.15, 137.86, 137.83, 137.77, 137.47, 137.19, 136.42, 134.48, 132.49, 132.33, 129.85, 129.81, 129.76, 129.02, 128.56, 128.44, 128.37, 128.34, 128.32, 128.29, 128.25, 128.19, 127.85, 127.82, 127.76, 127.75, 127.68, 127.55, 125.99, 101.28, 95.59, 88.02, 85.23, 81.98, 81.09, 78.88, 76.04, 75.95, 75.58, 74.84, 74.42, 74.39, 74.32, 73.59, 73.47, 72.48, 72.36, 71.33, 70.10, 69.92, 69.78, 68.67, 67.73, 67.41, 62.62, 21.14, 21.12.

Compound 17: a glycosyl donor 15 (1.42 g, 2.3 mmol) was mixed with a glycosyl donor 8 (1.11 g, 1.6 mmol) with an amino linking arm, and subjected to azeotropy with methylbenzene 3 times under the protection of nitrogen. Vacuumization was performed overnight by an oil pump. Afterwards, anhydrous DCM (100 ml) and an appropriate amount of molecular sieves were added. Stirring was carried out at the room temperature for 30 min followed by lowering the temperature to −78° C. After stirring was further performed for 30 min, an accelerator TMSOTf (37 μL) was added. The reaction solution was further stirred for 6 h. The reaction was monitored with TLC. After the complete consumption of the glycosyl donor, the reaction was quenched with triethylamine. The reaction solution was extracted with dichloromethane and a saturated sodium bicarbonate solution. An organic phase was separated and concentrated after drying with anhydrous sodium sulfate. The concentrated solution was purified with a silicagel column (petroleum ether/ethyl acetate, 4:1) to obtain the compound 17 (1.35 g, 1.2 mmol). $^1$H NMR (400 MHz, Chloroform-d) δ 7.48-6.97 (m, 35H, Ar—H), 5.64 (s, 1H, 1'-H), 5.55 (d, J=7.7 Hz, 2H, PhCH, 3'-H), 5.16 (d, J=10.3 Hz, 2H, 2Bn-H), 4.92 (d, J=10.2 Hz, 1H, Bn-H), 4.65 (t, J=12.3 Hz, 2H, 2Bn-H), 4.55 (t, J=10.5 Hz, 2H, 1-H, Bn-H), 4.50-4.40 (m, 4H, 2Cbz-H, 2Bn-H), 4.32 (d, J=10.8 Hz, 1H, 6a-H, Bn-H), 4.23 (t, J=9.4 Hz, 2H, 5'-H, Bn-H), 3.73 (ddt, J=37.9, 19.0, 9.3 Hz, 6H, 2-H, 4-H, 5-H, 6b-H, 4'-H, linker-OCH), 3.50 (d, J=9.7 Hz, 1H, 2'-H), 3.41 (q, J=8.7 Hz, 2H, 3-H, linker-OCH), 3.18 (q, J=11.6, 10.7 Hz, 4H, 6'ab-H, linker-NCH$_2$), 1.91 (s, 3H, Me), 1.70-1.34 (m, 4H, linker-CH$_2$), 1.22 (d, J=27.7 Hz, 2H, linker-CH$_2$).

Compound 18: the compound 17 (1.1 g, 0.96 mmol) was dissolved in absolute methanol (20 ml). Sodium methoxide (100 mg) was added. The reaction solution was stirred at 40° C. for 24 h. The reaction was monitored with TLC. After complete reaction of the raw materials, the reaction solution was neutralized to be neutral with Amberlite IR120 H$^+$ resin. The resin was filtered out. Purification was carried out with a silicagel column (petroleum ether/ethyl acetate, 3:1) after concentration to obtain the compound 18 (898 mg, 0.82 mmol). $^1$H NMR (400 MHz, Chloroform-d) δ 7.67-6.95 (m, 35H, Ar—H), 5.68 (s, 1H,1'-H), 5.62 (s, 1H, PhCH—H), 5.21 (d, J=11.2 Hz, 2H, Bn-H), 4.94 (d, J=10.1 Hz, 1H, Bn-H), 4.83 (d, J=11.3 Hz, 2H, Bn-H), 4.60 (t, J=11.1 Hz, 4H, 1-H, 1Bn-H, 2Cbz-H), 4.50 (t, J=10.5 Hz, 3H,3Bn-H), 4.39 (d, J=9.8 Hz, 1H, 6a-H), 4.29 (d, J=12.1 Hz, 1H, Bn-H), 4.25-4.08 (m, 2H, 3'-H, 5'-H), 3.79 (dq, J=18.3, 9.5 Hz, 5H, 2-H, 3-H, 4-H, 6b-H, linker-OCH), 3.65 (t, J=9.5 Hz, 1H, 4'-H), 3.57-3.37 (m, 3H,5-H, 2'-H, linker-OCH), 3.34-3.14 (m, 4H, 6'ab-H, linker-NCH$_2$), 2.50 (s, 1H, 3'-OH), 1.52 (ddt, J=22.4, 15.3, 7.9 Hz, 4H, linker-CH$_2$), 1.41-1.14 (m, 2H, linker-CH$_2$). $^{13}$C NMR (101 MHz, CDCl$_3$) δ 156.72, 156.22, 138.90, 138.05, 137.93, 137.66, 137.30, 129.03, 128.59, 128.49, 128.32, 128.28, 128.26, 128.14, 127.98, 127.89, 127.73, 127.68, 127.62, 127.54, 127.34, 125.99, 104.00, 101.23, 95.10, 82.28, 79.60, 79.03, 77.63, 77.42, 77.31, 77.10, 76.79, 75.65, 75.57, 74.63, 73.51, 73.40, 71.97, 69.62, 69.49, 68.81, 67.86, 67.21, 65.95, 50.53, 50.24, 47.05, 46.15, 29.74, 29.63, 27.96, 27.54, 23.33.

Example 5

Figure 5:
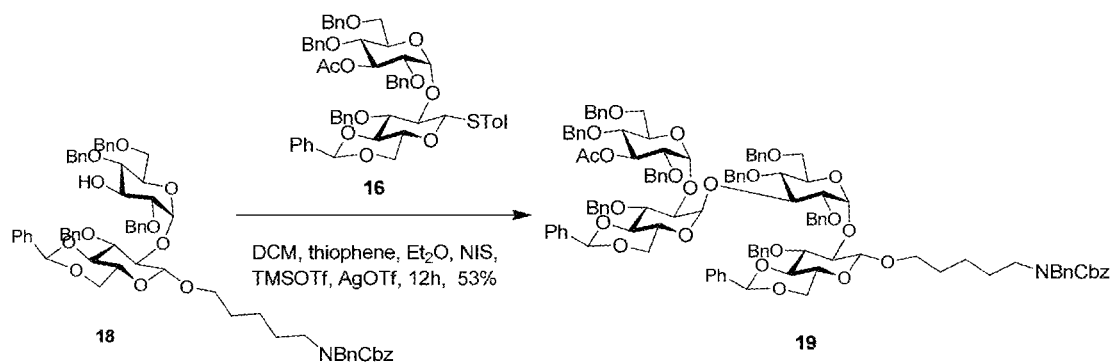
FIG. 5 shows synthesis of a tetrasaccharide compound 19 in Example 5.

Synthesis of a Tetrasaccharide 19 is as Shown in FIG. 5.

Compound 19: a disaccharide glycosyl donor 15 (287 mg, 0.3 mmol) was mixed with a disaccharide glycosyl donor 18 (230 mg, 0.12 mmol), and subjected to azeotropy with methylbenzene 3 times under the protection of nitrogen. Vacuumization was performed overnight by an oil pump. Afterwards, anhydrous DCM (2 ml), ether (4 ml) and thiophene (12.6 mmol), and an appropriate amount of molecular sieves were added. Stirring was carried out at the room temperature for 30 min followed by lowering the temperature to 0° C. After stirring was further performed for 30 min, accelerators NIS (135 mg) and AgOTf (26 mg) were added. The reaction solution was further stirred in an ice bath for 12 h. The reaction was monitored with TLC. The reaction solution was extracted with a 10% sodium thiosulfate solution and dichloromethane after complete consumption of the glycosyl donor. An organic phase was separated and concentrated after drying with anhydrous sodium sulfate. The concentrated solution was purified with a silicagel column (petroleum ether/ethyl acetate, 4:1) to obtain the compound 19 (121 mg, 0.064 mmol). $^1$H NMR (400 MHz, Chloroform-d) δ 5.81 (s, 1H, a1-H), 5.73 (t, J=9.7 Hz, 1H, c3-H), 5.63 (s, 1H, b1-H), 5.55 (d, J=5.6 Hz, 2H, 2PhCH), 5.19 (d, J=8.9 Hz, 3H, 1c-H, 2Bn-H), 4.90 (d, J=10.9 Hz, 1H, Bn-H), 4.79 (d, J=15.8 Hz, 3H, 3Bn-H), 4.54 (ddt, J=47.2, 27.9, 9.9 Hz, 13H, d1-H, a3-H, 2Cbz-H, 9Bn-H), 4.38-4.14 (m, 8H, d3-H, b5-H, c5-H, c6-H2, 3Bn-H), 4.03 (t, J=9.3 Hz, 1H, b3-H), 3.74 (td, J=30.8, 27.3, 8.7 Hz, 9H, a6-H2, a2-H, b4-H, d2-H, d5-H, c4-H, a5-H, linker-OCH), 3.49 (ddd, J=42.6, 21.7, 9.6 Hz, 6H, d6-H2, d4-H, b2-H, a2-H, a4-H), 3.20 (d, J=34.7 Hz, 5H, b6-H2, linker-NH$_2$, linker-OCH), 1.89 (s, 3H, Me). $^{13}$C NMR (101 MHz, CDCl$_3$) δ 169.61, 138.61, 138.32, 138.16, 138.02, 137.96, 137.68, 137.61, 137.34, 136.87, 130.92, 128.96, 128.80, 128.75, 128.69, 128.56, 128.48, 128.38, 128.32, 128.26, 128.21, 128.09, 128.03, 127.95, 127.86, 127.73, 127.66, 127.62, 127.59, 127.56, 127.51, 127.47, 127.25, 126.18, 125.99, 103.93, 101.22, 95.04, 94.72, 94.50, 82.61, 82.21, 79.44, 78.54, 78.31, 77.36, 77.04, 76.72, 76.25, 75.72, 75.49, 75.37, 75.18, 74.15, 73.44, 73.38, 73.16, 72.13, 71.40, 69.92, 69.43, 69.17, 68.91, 68.81, 68.16, 67.93, 67.18, 65.80, 65.58, 62.36, 50.48, 47.05, 46.15, 29.72, 29.55, 27.89, 27.49, 23.20, 21.09, 19.20, 13.74.

Example 6

Optimization of a 1,3-α-Cis-Glycosidic Bond Constructing System

1) Effects of Solvents on Construction of a 1,3-α-Cis-Glycosidic Bond

With reference to Example 5, the content of the 1,3-α-cis-glycosidic bond in the resulting product was determined through respectively replacing the solvents with the solvents shown in table 1. See table 1 for the results.

TABLE 1

Construction of a 1,3-α-cis-glycosidic bond with different solvent and additive systems

| Reaction conditions (c = 50 mM) | α/β |
| --- | --- |
| DCM, NIS, TMSOTf | 1:1.8 |
| DCM, 100 eq thiophene, NIS, TMSOTf | 5:1 |
| DCM:Et$_2$O = 1:3, NIS, TMSOTf | 4:1 |
| DCM:Et$_2$O = 1:3, 100 eq thiophene, NIS, TMSOTf | >10:1 |

2) Effects of Accelerators on Construction of a 1,3-α-Cis-Glycosidic Bond

With reference to Example 5, the content of the 1,3-α-cis-glycosidic bond in the resulting product was determined through respectively replacing the accelerators with the additives shown in table 1. See table 2 for the results.

TABLE 2

Construction of a 1,3-α-cis-glycosidic bond under different accelerator conditions

| Reaction conditions (c = 50 mM) | Yield | α/β |
| --- | --- | --- |
| DCM:Et$_2$O = 1:3, 100 eq thiophene, NIS, TMSOTf | 44% | >10:1 |
| DCM:Et$_2$O = 1:3, 100 eq thiophene, NIS, AgOTf | 46% | >10:1 |
| DCM:Et$_2$O = 1:3, 100 eq thiophene, NIS, AgOTf, TMSOTf | 59% | >10:1 |

Example 7

Figure 6:
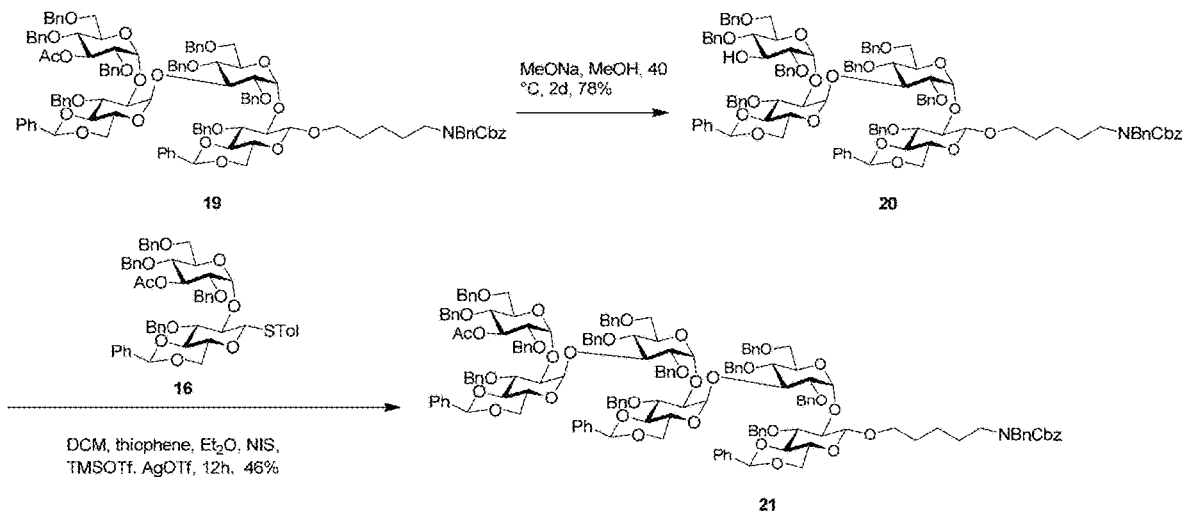
FIG. 6 shows synthesis of a saccharide compound 21 in Example 7.

Synthesis of a Hexaose 21 was as Shown in FIG. 6.

The tetrasaccharide compound 19 reacted in the presence of methanol and sodium methoxide for two days to remove 3''''-OA to obtain a tetrasaccharide compound 20. Afterwards, the compound 20 as a glycosyl receptor reacted with a disaccharide donor 16 under the catalysis of an accelerator Lewis acid to obtain a hexaose compound 21.

Compound 20: the compound 19 (90 mg, 0.047 mmol) was dissolved in a mixed solvent of methanol (9 ml) and ethyl acetate (1 ml). Sodium methoxide (30 mg) was added. Stirring was carried out at 40° C. for 2 d in the reaction. The reaction was monitored with TLC. After complete reaction of the raw materials, the reaction solution was neutralized to be neutral with Amberlite IR120 W resin. The resin was filtered out. Purification was carried out with a silicagel column (petroleum ether/ethyl acetate, 3:1) after concentration to obtain the compound 21 (68 mg, 0.037 mmol). $^1$H NMR (400 MHz, Chloroform-d) δ 5.79 (d, J=3.4 Hz, 1H, a1-H), 5.68 (d, J=5.3 Hz, 1H, b1-H), 5.55 (d, J=2.7 Hz, 2H, 2PhCH), 5.19 (d, J=9.2 Hz, 2H, 2Bn-H), 5.06 (d, J=3.4 Hz, 1H, c1-H), 4.97 (d, J=11.1 Hz, 1H, Bn-H), 4.79 (ddd, J=21.1, 11.9, 7.4 Hz, 4H, 4Bn-H), 4.68-4.44 (m, 11H, d1-H, b3-H, a4-H, 6Bn-H, 2Cbz-H), 4.46-4.37 (m, 2H, 2Bn-H), 4.36-4.23 (m, 6H, d3-H, a5-H, 2Bn-H, 6-H2), 4.17 (t, J=9.3 Hz, 1H, c3-H), 4.12-4.01 (m, 2H, c4-H, a3-H), 3.87-3.68 (m, 6H, d2-H, b4-H, c5-H, 6-H2, linker-OCH), 3.68-3.62 (m, 2H, a2-H, d5-H), 3.60 (d, J=9.4 Hz, 2H, b2-H, b5-H), 3.45 (dd, J=11.1, 3.1 Hz, 1H, 6-H), 3.40-3.33 (m, 2H, c2-H, d4-H), 3.30-3.11 (m, 6H, linker-NCH$_z$, linker-OCH, 6-H, 6-H2), 1.56-1.34 (m, 4H, 2linker-CH$_2$), 1.23-1.06 (m, 4H, linker-CH$_2$). $^{13}$C NMR (101 MHz, CDCl$_3$) δ 156.70, 156.18, 138.86, 138.70, 138.24, 138.20, 138.14, 138.07, 138.01, 137.93, 137.78, 137.62, 137.44, 137.31, 136.91, 129.79, 129.23, 129.01, 128.81, 128.71, 128.69, 128.65, 128.59, 128.50, 128.42, 128.32, 128.29, 128.25, 128.22, 128.20, 128.16, 128.15, 128.02, 127.97, 127.88, 127.84, 127.75, 127.66, 127.62, 127.60, 127.56, 127.48, 127.42, 127.35, 126.16, 126.00, 103.92, 102.01, 101.26, 101.21, 95.76, 95.36, 94.59, 82.79, 82.11, 81.12, 79.58, 79.43, 78.86, 78.25, 78.07, 77.40, 77.28, 77.08, 76.76, 75.35, 75.31, 74.79, 74.67, 74.47, 73.85, 73.57, 73.45, 73.39, 73.29, 71.93, 71.75, 69.92, 69.23, 68.77, 68.21, 67.90, 67.20, 65.81, 62.70, 50.50, 50.20, 47.05, 46.13, 29.74, 29.58, 27.91, 27.50, 23.23.

Compound 21: a disaccharide donor 15 (60 mg, 0.064 mmol) and a tetrasaccharide receptor 20 (50 mg, 0.027 mmol) were subjected to azeotropy with methylbenzene 3 times under the protection of nitrogen. Vacuumization was performed overnight by an oil pump. Afterwards, anhydrous DCM (0.5 ml), ether (1 ml) and thiophene (0.6 ml), and an appropriate amount of molecular sieves were added. Stirring was carried out at the room temperature for 30 min followed by lowering the temperature to 0° C. After stirring was further performed for 30 min, accelerators NIS (29 mg) and AgOTf (3 mg) were added. The reaction solution was further stirred in an ice bath for 12 h. The reaction was monitored with TLC. After the complete consumption of the glycosyl donor, the reaction solution was extracted with a 10% sodium thiosulfate solution and dichloromethane. An organic phase was separated and concentrated after drying with anhydrous sodium sulfate. The concentrated solution was purified with a silicagel column (petroleum ether/ethyl acetate, 4:1) to obtain the compound 21 (33.4 mg, 0.012 mmol). $^1$H NMR (400 MHz, Chloroform-d) δ 5.91 (s, 1H, a1-H), 5.75 (d, J=12.4 Hz, 2H, b1-H, b3-H), 5.58 (s, 2H, c1-H, PhCH—H), 5.52 (s, 1H, PhCH), 5.50 (s, 1H, PhCH), 5.36 (s, 1H, d1-H), 5.22 (s, 3H, e1-H, 2Bn-H), 4.94-4.72 (m, 7H, 7Bn-H), 4.53 (ddt, J=44.2, 17.1, 10.5 Hz, 18H, f1-H, c3-H, d3-H, 2Cbz-H, 13Bn-H), 4.34 (dt, J=23.0, 10.9 Hz, 7H, f4-H, 4Bn-H, 6-H2), 4.22 (d, J=11.1 Hz, 2H, f5-H, b5-H), 4.08 (q, 1=11.8, 9.3 Hz, 3H, a3-H, e3-H, 6-H), 3.90 (d, J=9.6 Hz, 1H, a2-H, 6-H), 3.88-3.64 (m, 10H, f2-H, f3-H, b4-H, d4-H, e4-H, a5-H, c3-H, 6-H2, linker-OCH), 3.53 (dp, J=32.8, 11.4, 10.7 Hz, 10H, a4-H, c2-H, b2-H, e2-H, c5-H, d2-H, d5-H, e5-H, 6-H2), 3.36-3.10 (m, 5H, b6-H2, linker-NCH$_2$, linker-OCH), 1.93 (s, 3H, Me), 1.57-1.40 (m, 4H, 2linker-CH$_2$), 1.23-1.11 (m, 2H, linker-CH$_2$). $^{13}$C NMR (176 MHz, CDCl$_3$) δ 206.98, 192.41, 169.83, 169.74, 156.70, 138.41, 137.94, 137.90, 137.71, 137.29, 136.90, 136.44, 134.48, 130.93, 129.77, 129.02, 128.86, 128.84, 128.62, 128.57, 128.50, 128.43, 128.38, 128.34, 128.28, 128.24, 128.05, 128.01, 127.91, 127.87, 127.75, 127.70, 127.65, 127.59, 127.56, 127.53, 127.50, 127.47, 127.45, 127.40, 127.37, 127.33, 127.29, 126.24, 126.21, 126.16, 126.01, 103.95, 101.28, 101.18, 94.82, 94.36, 94.12, 93.96, 82.53, 82.21, 79.40, 78.67, 77.22, 77.04, 76.86, 76.16, 75.78, 75.59, 75.38, 75.20, 74.89, 74.27, 74.18, 73.45, 73.42, 73.39, 73.27, 72.97, 72.13, 71.17, 70.51, 70.07, 69.81, 69.24, 68.98, 68.80, 68.60, 68.15, 67.83, 67.20, 65.83, 62.13, 50.47, 50.16, 47.03, 46.10, 30.96, 29.73, 29.54, 27.88, 27.47, 23.20, 22.72, 21.13, 21.11, 14.15.

A series of oligosaccharide derivatives of *Helicobacter pylori* serotype O2 such as octasaccharide, decasaccharide, and dodecaose may be synthesized according to this method.

An oligosaccharide chain may extend from a reducing end to a non-reducing end in a +2 saccharide mode, including two steps: 1) removing a lipid group at the non-reducing end from the oligosaccharide with a linking arm at the reducing end; and 2) performing glycosylation with a disaccharide donor 16.

Method for removing the lipid group at the non-reducing end from an oligosaccharide: a compound (about 50 mg) was dissolved in methanol (10 to 15 ml), and a small amount of ethyl acetate or tetrahydrofuran may be added appropriately to enhance solubility; sodium methoxide (20 to 30 mg) was added; the reaction solution was stirred at 40° C. for 12 h to 2 d; the reaction process was monitored with TLC; after the complete reaction of the raw materials, the reaction solution was neutralized to be neutral with Amberlite IR120 W resin; the resin was filtered out; and purification was carried out with a silicagel column after concentration.

Method for glycosylation with a disaccharide 16 as a glycosyl donor: a glycosyl donor and a glycosyl receptor were subjected to azeotropy with methylbenzene three times under the protection of nitrogen; vacuumization was performed overnight by an oil pump; the reactant was dissolved in a mixed solvent of dichloromethane and ether (1:1), and 100-fold equivalents of thiophene (relative to the glycosyl donor) and an appropriate amount of molecular sieves were added at the same time; one or more of NIS and AgOTf, and TMSOTf and TfOH were added as accelerators, wherein the reaction concentration was 0.02 M (relative to the glycosyl donor), and the reaction time is 12 to 24 h; the reaction process was monitored with TLC; after the complete reaction of the glycosyl donor, the reaction solution was extracted with a 10% sodium thiosulfate solution, dichloromethane, and a saturated sodium bicarbonate solution; an organic phase was separated and dried with anhydrous sodium sulfate; and purification was carried out with a silicagel column after concentration to obtain a new oligosaccharide compound.

Example 7

Deprotection of Disaccharide, Tetrasaccharide, and Hexaose

Figure 7:
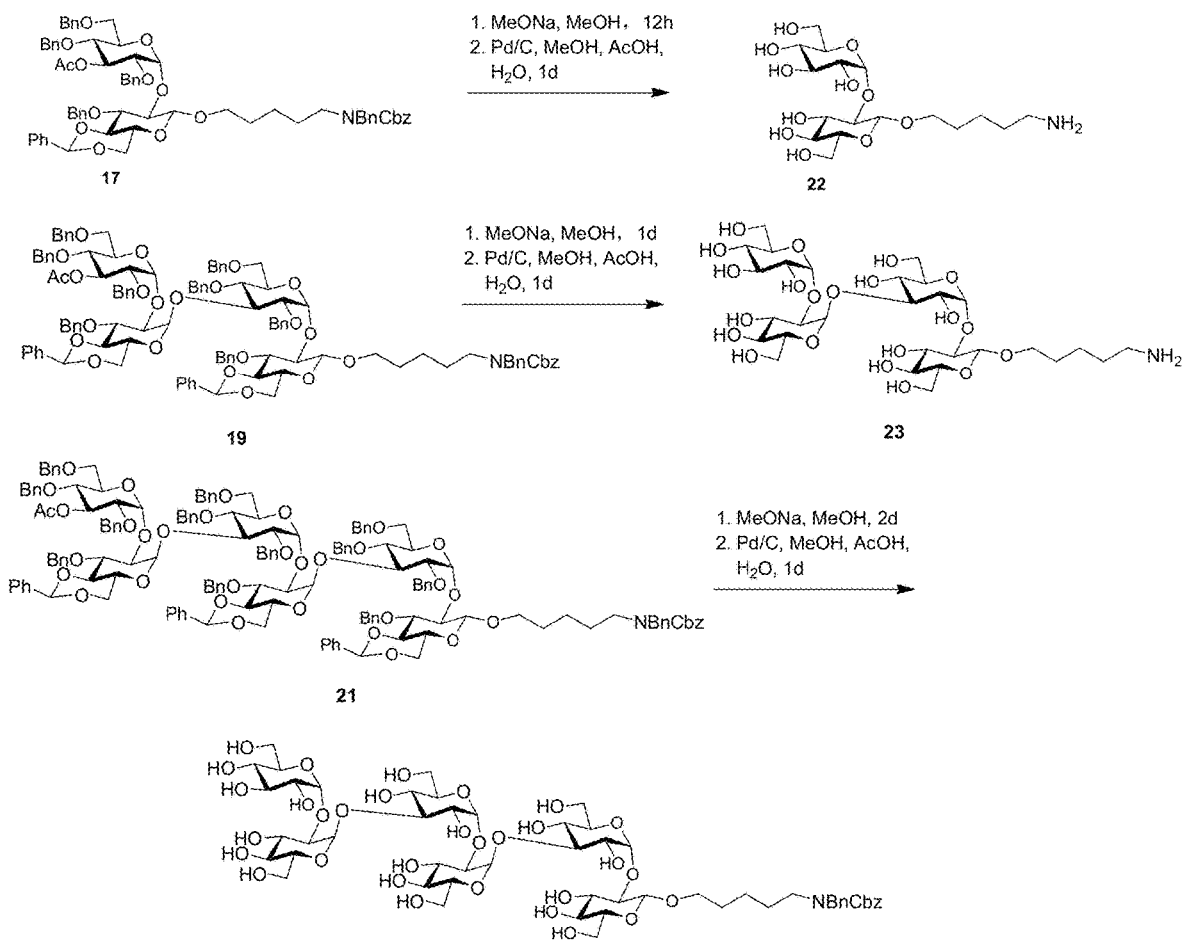
FIG. 7 shows deprotection of a disaccharide, a tetrasaccharide, and a hexaose.
Figure 8:
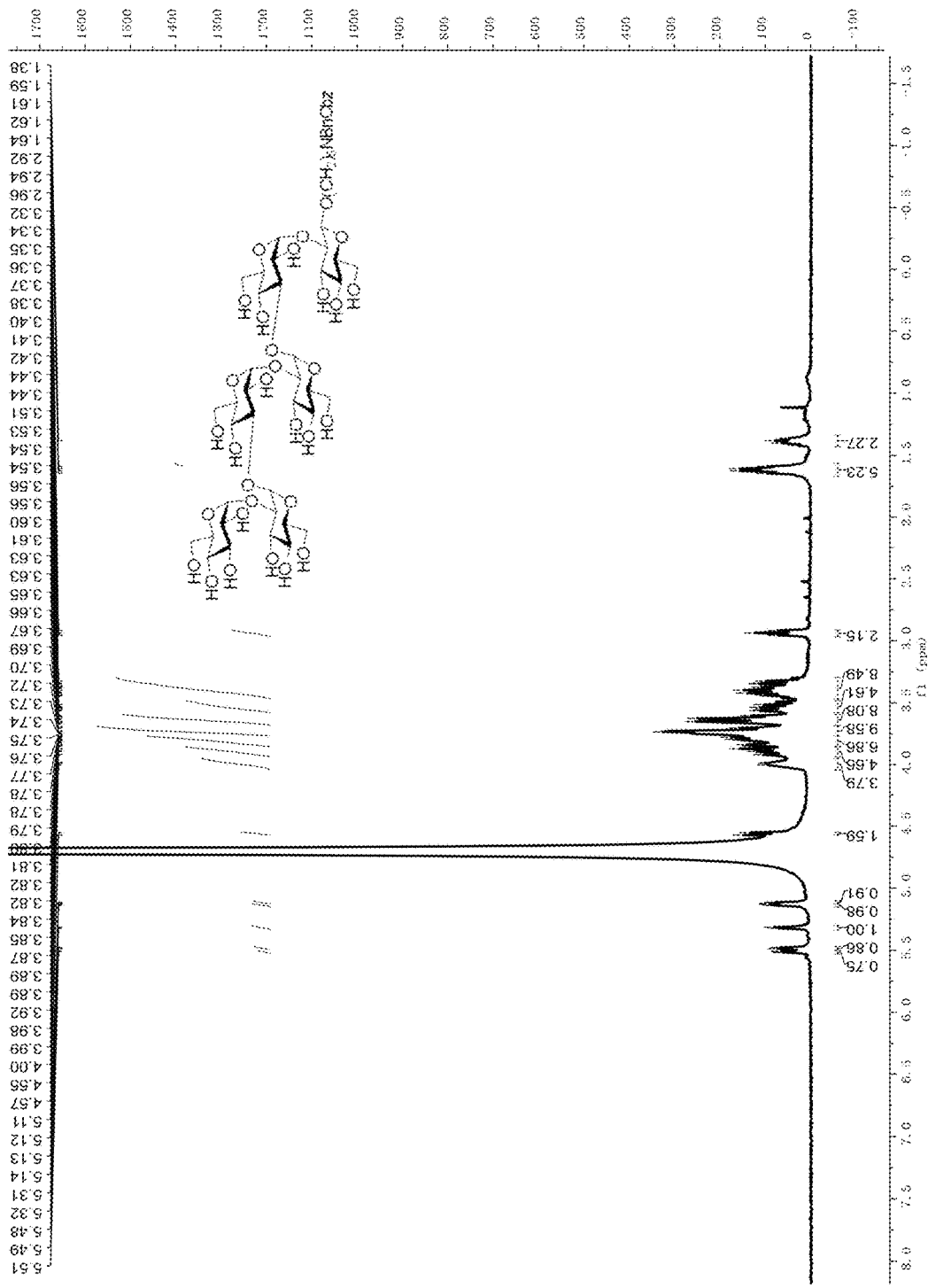
FIG. 8 shows hydrogen spectrum of a compound 24.
Figure 9:
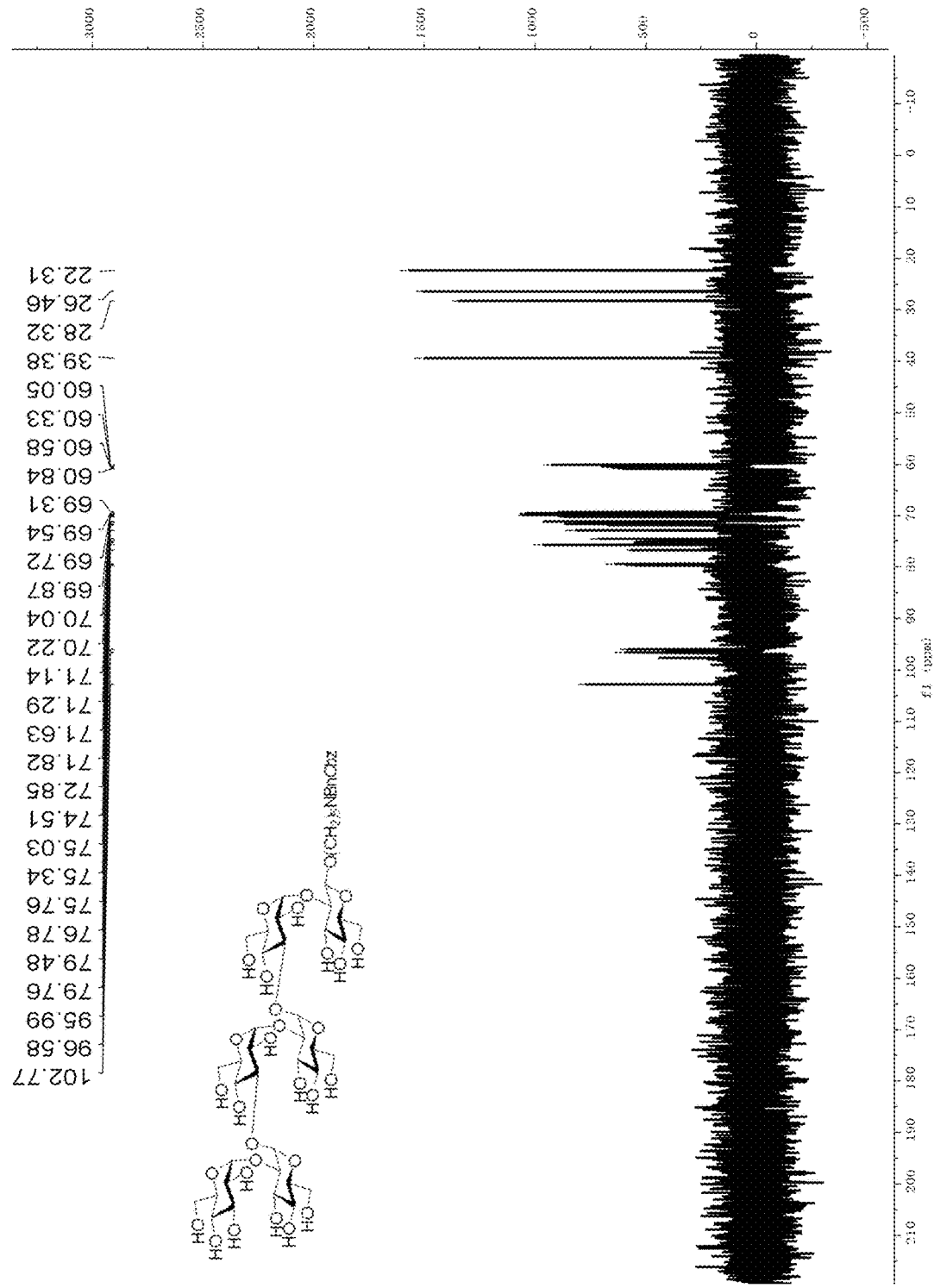
FIG. 9 shows carbon spectrum of the compound 24.
Figure 10:
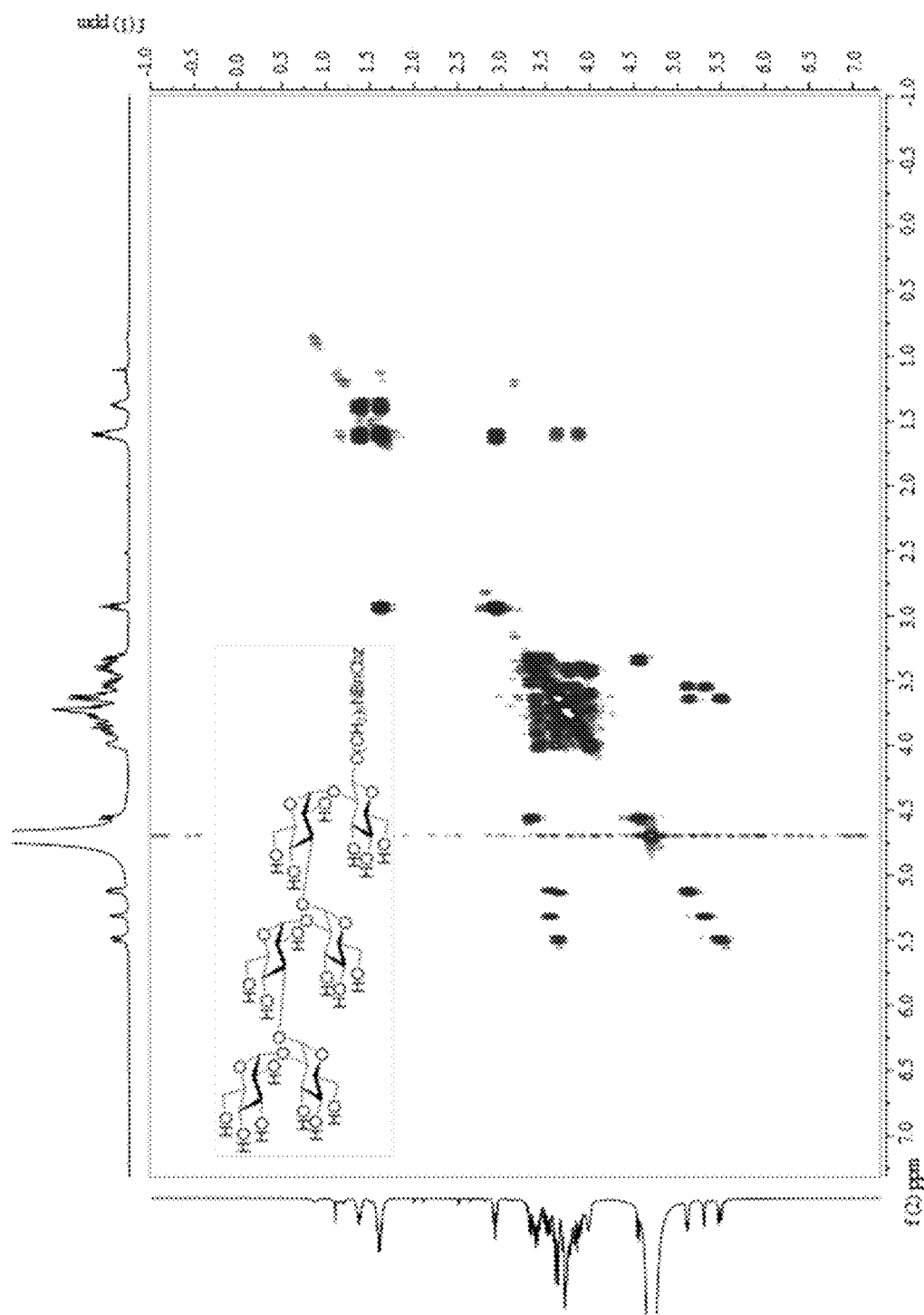
FIG. 10 shows hydrogen-hydrogen correlation spectrum of the compound 24.
Figure 11:
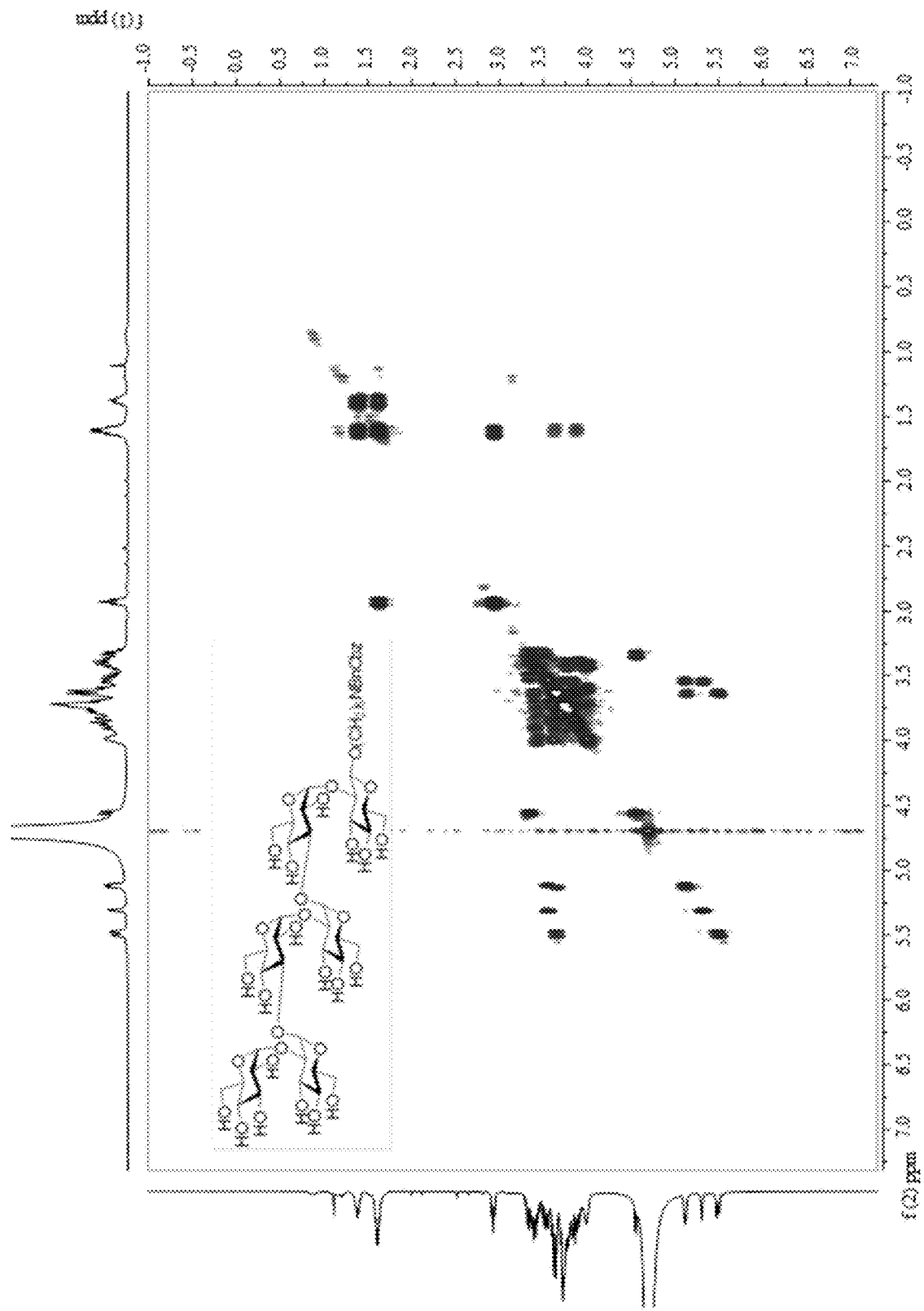
FIG. 11 shows carbon-hydrogen correlation spectrum of the compound 24.

As shown in FIG. 7, deprotection of a disaccharide, a tetrasaccharide, and a hexaose was divided into two steps. First, acetyl at the non-reducing end was deprotected under alkaline conditions. Second, all aromatic groups were hydrogenated under catalysis of palladium carbon to obtain the disaccharide, tetrasaccharide, and hexaose with reducing ends assembled with five-carbon amino linking arms Method for removing disaccharide acetyl at the non-reducing end: a compound was dissolved in a mixed solvent of methanol and ethyl acetate (9:1) with a concentration of 0.02M; 0.5 equivalents of sodium methoxide (relative to the raw materials) were added; the reaction solution was stirred at 40° C. for 12 h to 2 d; the reaction process was monitored with TLC; after the complete reaction of the raw materials, the reaction solution was neutralized to be neutral with Amberlite IR120 H$^+$ resin; the resin was filtered out; and purification was carried out with a silicagel column after concentration.

Method for hydrogenation: a compound (6 to 10 mg) was dissolved in a mixed solution of isobutanol (3 ml), methanol (1 ml), and water (1 ml); glacial acetic acid (0.1 ml) and palladium carbon (50 mg) were added; the reaction solution reacted in a medium-pressure hydrogen reactor under the pressure of 0.4 MPa for 12 h; after complete reaction of the raw materials, the reaction solution was filtered with diatomite; and purification was carried out with a C18 pillaret to obtain a target compound.

Specific test and operation steps are as follows.

Compound 22: a deprotected disaccharide compound 22 was produced by steps of acetyl removal and hydrogenation with the disaccharide compound 17 as a raw material. $^1$H NMR (400 MHz, Deuterium Oxide) δ 5.37 (d, J=3.8 Hz, 1H, 1'-H), 4.61 (d, J=7.9 Hz, 1H, 1-H), 4.05 (dt, J=10.2, 3.3 Hz, 1H, 5'-H), 4.00-3.89 (m, 2H, 6-H, linker-OCH), 3.81 (d, J=3.4 Hz, 2H, 6'-H2), 3.77-3.67 (m, 3H), 3.58 (t, J=9.0 Hz, 1H, 4-H), 3.52 (dd, J=9.9, 3.9 Hz, 1H, 2'-H), 3.49-3.36 (m, 4H, 4'-H, 2-H, 3-H, 5-H), 3.02 (t, J=7.6 Hz, 2H, linker-NCH$_2$), 1.70 (q, J=7.2 Hz, 4H, 2linker-CH$_2$), 1.57-1.39 (m, 2H, linker-CH$_2$). $^{13}$C NMR (101 MHz, D$_2$O) δ 102.77, 97.61, 77.02, 75.71, 74.50, 72.91, 71.63, 71.43, 70.18, 69.84, 69.30, 60.81, 60.23, 39.37, 28.28, 26.43, 22.28.

Compound 23: a deprotected tetrasaccharide compound 23 was produced by steps of acetyl removal and hydrogenation with the tetrasaccharide compound 19 as a starting material. $^1$H NMR (400 MHz, Deuterium Oxide) δ 5.44 (d, J=3.6 Hz, 1H, a1-H), 5.28 (d, J=3.9 Hz, 1H, b1-H), 5.08 (d, J=3.7 Hz, 1H, c1-H), 4.53 (d, J=8.1 Hz, 1H, d1-H), 3.96 (d, J=9.6 Hz, 2H, a3-H, c4-H), 3.92-3.65 (m, 12H, linker-OCH, b3-H, c3-H, d3-H, b4-H, d5-H, 6*6-H), 3.65-3.44 (m, 7H, linker-OCH, a2-H, a5-H, b2-H, c2-H, 2*6-H), 3.43-3.22 (m, 5H, a4-H, b5-H, d2-H, d4-H, c5-H), 2.90 (t, J=7.6 Hz, 2H, linker-NCH$_2$), 1.58 (q, J=7.4 Hz, 4H, linker-CH$_2$), 1.36 (q, J=8.0 Hz, 2H, linker-CH$_2$). $^{13}$C NMR (101 MHz, D$_2$O) δ 102.75, 97.71, 96.49, 95.98, 79.83, 76.87, 75.74, 75.37, 74.50, 72.84, 71.82, 71.54, 71.28, 70.21, 69.88, 69.51, 69.29, 60.84, 60.32, 39.38, 28.30, 26.45, 22.29.

Compound 24: a deprotected hexaose compound 24 was produced by steps of acetyl removal and hydrogenation with the hexaose compound 21 as a starting raw material. $^1$H NMR (400 MHz, Deuterium Oxide) δ 5.51 (d, J=3.7 Hz, 1H, a1-H), 5.48 (d, J=3.7 Hz, 1H, b1-H), 5.31 (d, J=3.9 Hz, 1H, c1-H), 5.13 (d, J=3.8 Hz, 1H, d1-H), 5.11 (d, J=3.7 Hz, 1H, e1-H), 4.55 (d, J=8.0 Hz, 1H, f1-H), 4.09-3.25 (m, 38H, 6*2-H, 6*3-H, 6*4-H, 6*5-H, 6*6-H2, linker-OCH$_2$), 2.93 (t, J=7.6 Hz, 2H, linker-NCH$_2$), 1.61 (h, J=6.9, 6.2 Hz, 4H, linker-CH$_2$), 1.43-1.30 (m, 2H, linker-CH$_2$). $^{13}$C NMR (101 MHz, D$_2$O) δ 102.77, 96.58, 95.99, 79.76, 79.48, 76.78, 75.76, 75.34, 75.03, 74.51, 72.85, 71.82, 71.63, 71.29, 71.14, 70.22, 70.04, 69.87, 69.72, 69.54, 69.31, 60.84, 60.58, 60.33, 60.05, 39.38, 28.32, 26.46, 22.31. The corresponding NMR spectrum is as shown in FIGS. 8-11.

Example 8

Optimization of Preparing Monosaccharide Building Blocks

For producing glucose building blocks with C-2 and C-3 being hydroxyl, respectively, starting from commercially available D-glucose, acetyl groupss on hydroxyl groups of the glucose were protected with acetic anhydride and sodium acetate at high temperature. Afterwards, most of peracetyl glucoses 108 obtained by crystallization were β-anomers, and thereafter, peracetyl glucose reacted with ethanethiol with the help of Lewis acid to obtain glucosinolate glucose 109. The remaining four acetyl groups were further hydrolyzed with sodium methoxide to obtain 110. The hydroxyl groups at positions 4, 6 of glucosinolate glucose 110 were protected with benzylidene to obtain glucosinolate glucose 107 with hydroxyl groups at positions 2, 3 vacated.

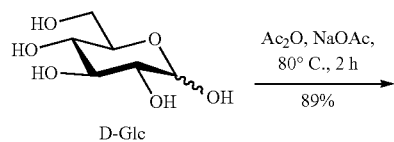

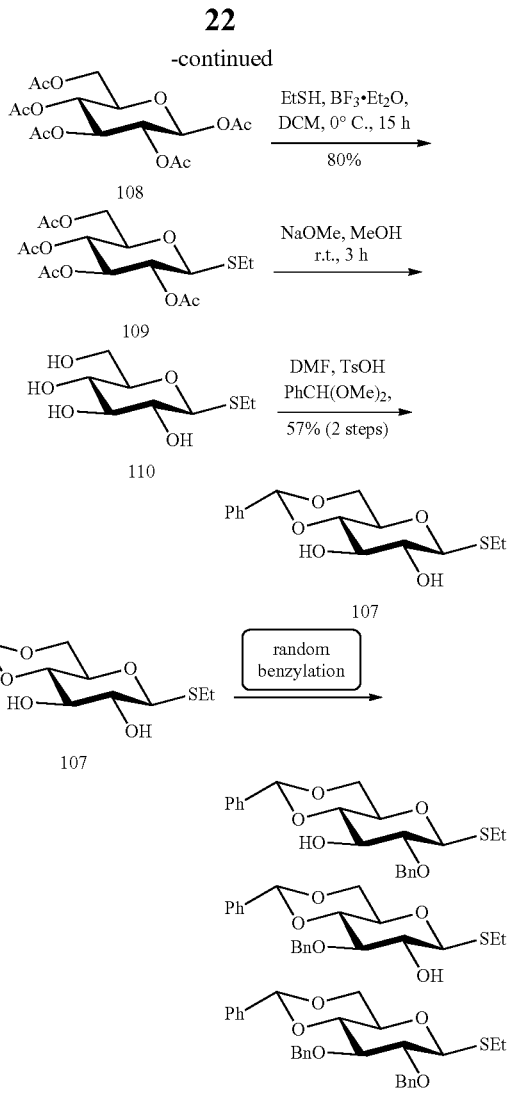

As positions C2 and C3 of glucose were similar in the properties, and cannot be obtained with the compound 107 through random benzylation. In this case, we need to re-design a saccharide building block path, and need to distinguish the structures of C-2 and C-3 from the start. To this end, we selected commercially available diacetone glucose as a starting material to re-design a reaction path. As compared with D-glucose selected in a previous design path, the greatest advantage of diacetone glucose lies in that a hydroxyl was retained at C-3, which distinguished the properties of the hydroxyl at C-2 from that at C-3. Hence, we re-designed saccharide building blocks, selected the commercially available diacetone glucose preferably as the starting material, and re-synthesized two saccharide building blocks for assembling O-Antigen oligosaccharides of *Helicobacter pylori* serotype O2 (corresponding to Example 1 and Example 2 respectively).

Example 9

Optimization of Glycosylation

The conditions for connecting tetrasaccharide were further explored on the basis of the presence of a disaccharide 124 and a disaccharide 138. We first tried glycosylation in pure dichloromethane, and obtained a tetrasaccharide 133 by reaction between most common iodosuccinimide and a Lewis acid trimethylsilyl triflate. However, unfortunately, the selectivity of the reaction was insufficient, and the selectivity of α/β was only 1:1.8. For obtaining more α-configured tetrasaccharide 133 as required by a target compound as much as possible, we tried various solvents, finding that adding an appropriate amount of ether into a reactive solvent can improve α-configuration moderately. For example, after the reactive solvent was replaced with a 31% mixed solvent of dichloromethane and ether (1:3), the selectivity of α-configuration of the tetrasaccharide was increased by 8 times, achieving the result of α/β being 4:1. However, the yield was reduced. Through adding 100-fold equivalents of thiophene (relative to the glycosyl donor) in a mixed solvent of dichloromethane and ether, it was found that the proportion of α-configuration in the resulting tetrasaccharide was further increased, i.e. achieving α/β>10:1, which satisfied the requirements for experiments in terms of selectivity. However, the reaction yield was low, only 44%. For trying improving the yield of the glycosylation, we tried different accelerators for glycosylation, including iodosuccinimide and Lewis acid trimethylsilyl triflate, trifluoromethanesulfonic acid or silver triflate, and the like, and combined use of a plurality of accelerators, finally finding that with a glucosinolate 124 as a glycosyl donor, aided with iodosuccinimide, silver triflate, and trimethylsilyl triflate together as accelerators, when reacting in a mixed solvent of DCM and ether (1/3) and a solvent added with thiophene, a tetrasaccharide compound 133 having α/β of 10:1 could be obtained with the yield of 59%.

TABLE 3

Optimization of conditions for synthesizing tetrasaccharide compound 133

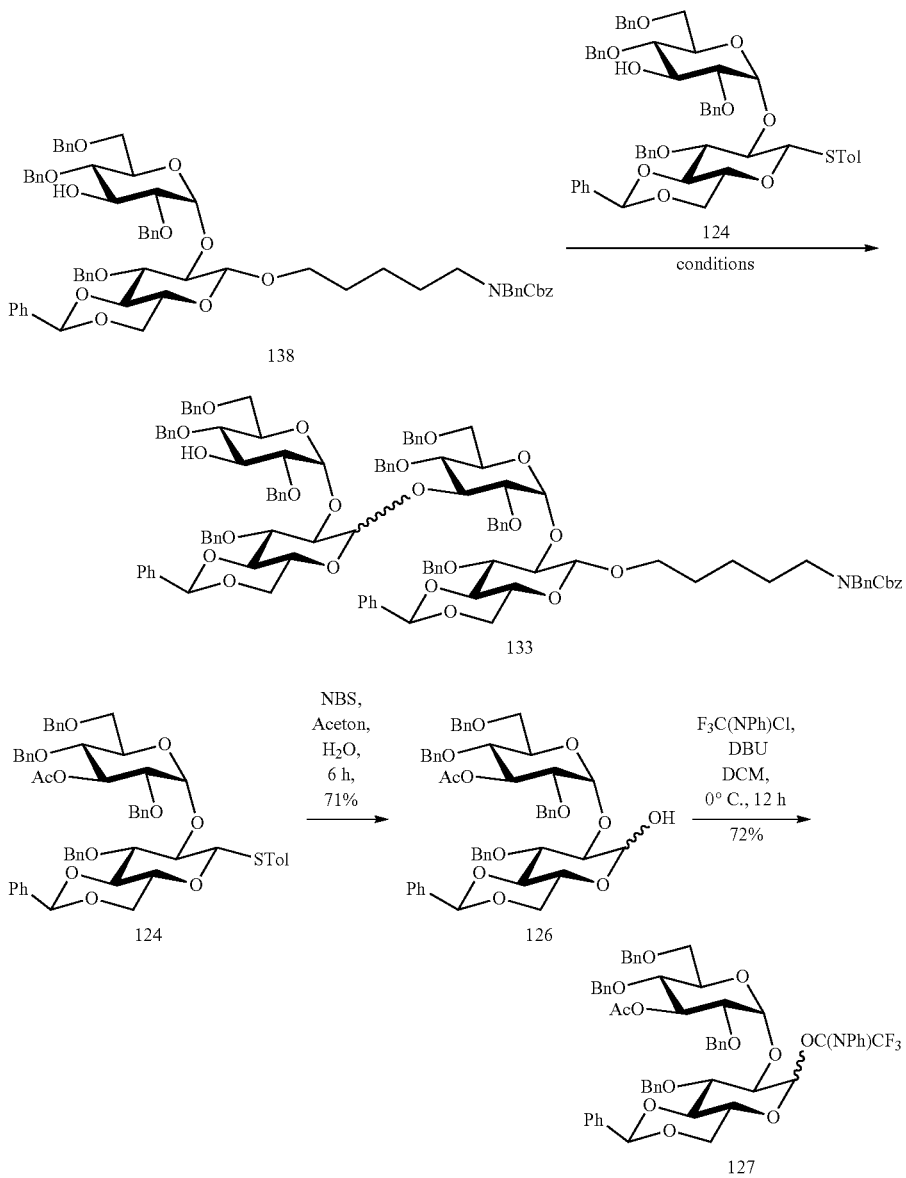

| No. | Condition | Yield | α/β |
|---|---|---|---|
| 1 | 124, DCM, NIS, TMSOTf | 66% | 1:1.8 |
| 2 | 124, DCM:Et$_2$O = 1:3, NIS, TMSOTf | 46% | 4:1 |

TABLE 3-continued

| | | | |
|---|---|---|---|
| 3 | 124, DCM:Et$_2$O = 1:3, 100 eq thiophene, NIS, TMSOTf | 44% | >10:1 |
| 4 | 124, DCM:Et$_2$O = 1:3, 100 eq thiophene, NIS, AgOTf | 46% | >10:1 |
| 5 | 124, DCM:Et$_2$O = 1:3, 100 eq thiophene, NIS, AgOTf, TMSOTf | 59% | >10:1 |
| 6 | 127, DCM:Et$_2$O = 1:3, 100 eq thiophene, TMSOTf | 62% | >10:1 |

For further improving the yield of reaction and α-stereoselectivity, we optimized the reaction of tetrasaccharide to some extent. The two major optimization routes were as follows: 1) thioglycoside on the disaccharide compound 124 can be activated with iodosuccinimide and Lewis acid for glycosylation, but was quite low in activation efficiency, the equivalent of accelerators was increased gradually, but inactivated receptors could still be recycled after glycosylation, and to this end, replacing the thioglycoside with a leaving group having better reactivity was, after all, a method for improving the synthesis yield of the tetrasaccharide; and 2) in addition, the inventor found through experiments that introducing a strong electron-withdrawing ester group on a donor can improve α-stereoselectivity of the glycosylation. Thus, introducing an ester group on the disaccharide donor may be taken into consideration to improve the α-stereoselectivity of the tetrasaccharide reaction.

Nevertheless, according to the method in table 3 (no. 6), the yield of the tetrasaccharide obtained with 127 as the donor was only 62%, and the α-stereoselectivity could also reach α/β>10:1. Although a disaccharide TFAI donor 137 had a little bit higher yield than the disaccharide thioglycoside donor 124, it was not significantly improved in the α-stereoselectivity, only higher by 2%. Moreover, two-step reaction was required from 124 to 127, and the yield was only 49%. As compared with the proportion of saccharide lost, the improved yield of a tetrasaccharide compound 133 seemed to be insignificant. From the perspective of overall synthesis, this was unworthy.

For introducing a lipid group on the disaccharide donor, the most readily conceivable manner was to open a benzylidene ring on a glucose residue at the reducing end of the disaccharide 124 first, thereby vacating hydroxyl groups at positions C-4 and C-6 to protect ester groups. As there were many hydrophobic groups on 124 and they were insoluble in an aqueous phase, benzylidene was hydrolyzed with trifluoroacetic acid in dichloromethane to obtain a 2-hydroxy compound 139. Thereafter, the vacated hydroxyl groups were protected with benzoyl groups to obtain a compound 140. The overall yield of the two-step reaction was 61%.

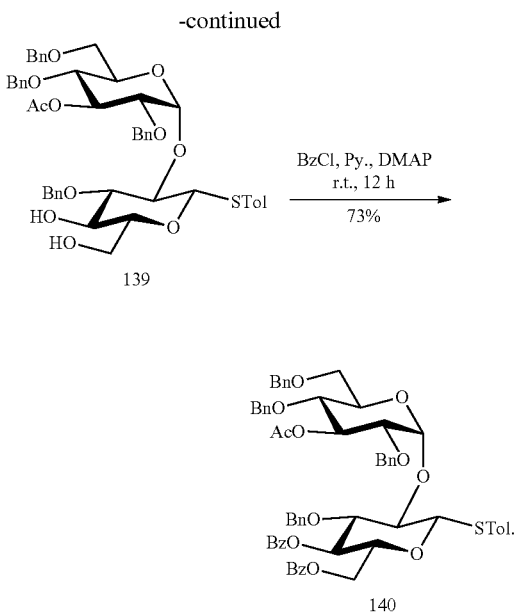

Next, the newly synthesized disaccharide donor 140 was used to react with a disaccharide receptor 138, finding that the donor 140 could not be inactivated by an accelerator. 140 could not be inactivated either by increasing the reaction temperature to 40° C. or increasing the amount of the accelerator. 140 was neither hydrolyzed nor reacted with the receptor during the reaction. Also, sufficient 140 could be recycled after the reaction. The inventor speculated there are two reasons for difficult activation of 140: 1) thioglycoside was stable per se, and this could not be observed from incomplete activation when 124 was used as a donor; 2) benzoyl had a strong electron-withdrawing capability, thereby reducing the electron cloud density at an end group position such that the glycosyl donor was passivated. Thus, for improving the reactivity of 140, thioglycoside must be replaced with a leaving group having better reactivity. Similar to the process from 124 to 127, 140 also experienced the same two-step reaction to obtain a glycosyl TFAI donor 142.

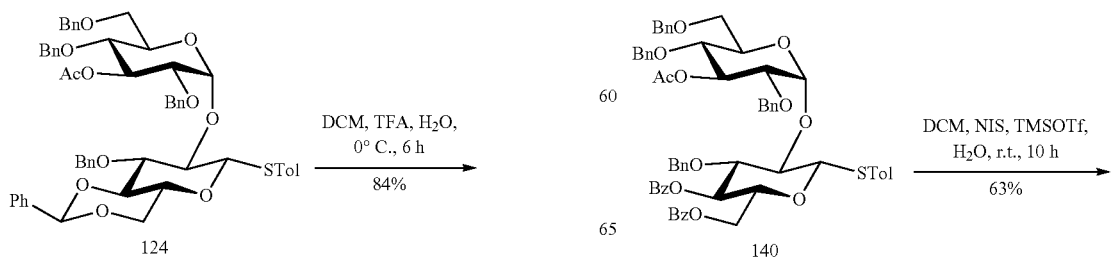

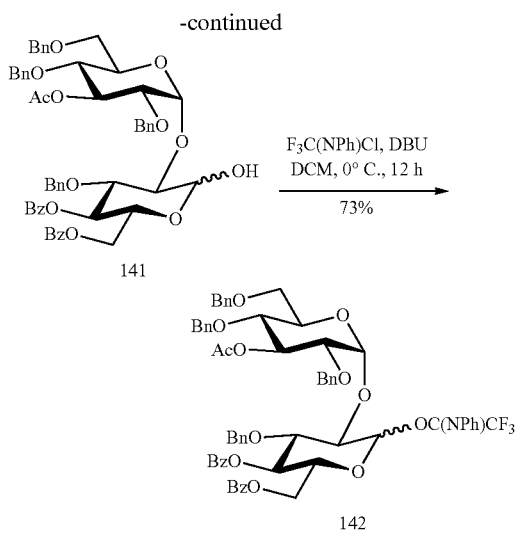

Subsequently, the donor 142 and the glycosyl receptor 138 were used for glycosylation to obtain a tetrasaccharide. Trimethylsilyl triflate were used as an accelerator to obtain a purely α-stereoselective tetrasaccharide compound 143. This was also benefited from the remote action of benzoyl.

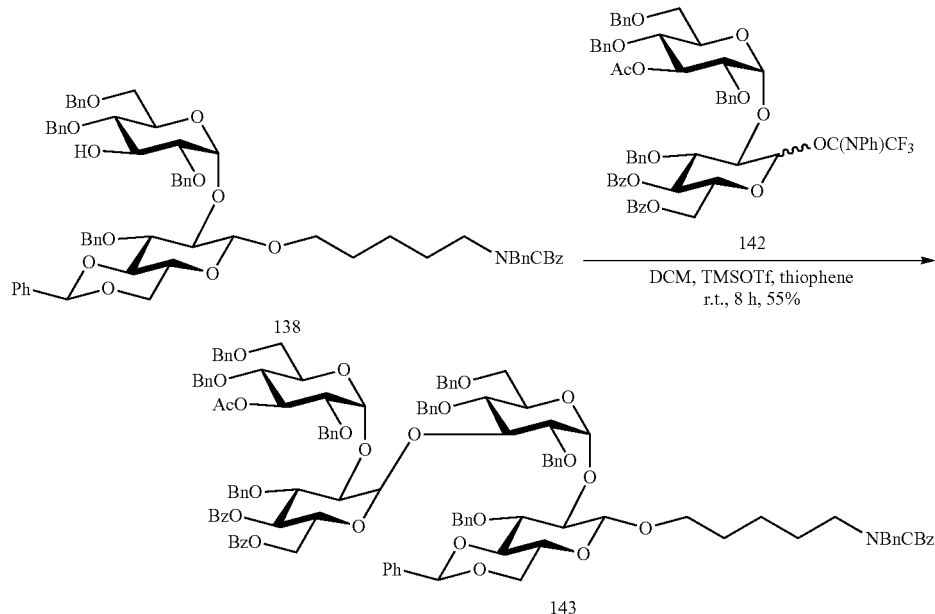

Nevertheless, from the aspect of stereoselectivity, the benzoyl disaccharide donor 142 exhibited excellent selectivity during glycosylation. However, from the aspect of efficiency of the synthesis path, the improvement made little sense. We assumed that the disaccharide donors were not lost during glycosylation, and could be recycled except those participating in reaction. In this case, discussion of the efficiency of glycosylation depended on the disaccharide donors. We considered the utilization efficiency from the disaccharide 124 to the tetrasaccharide 133 or to tetrasaccharide 143. The overall yield of 133 obtained from direct glycosylation of the thioglycoside disaccharide 124 was 53%, (59%×90%). The overall yield of 133 obtained from glycosylation of the receptor 138 and the glycosyl TFAI donor 127 was 28.5%, (71%×72%×62%×90%). The overall yield of 143 obtained from glycosylation of the benzyloxy glycosyl donor 142 was only 15.5% (84%×73%×63%×73%×55%×100%) in the third approach. Accordingly, based on the efficiency of glycosylation, we still selected the method of which the yield was not the highest during glycosylation, but the α-stereoselectivity was good, the overall path was the shortest, and the overall yield was far ahead another two paths. Thus, we completed the synthesis of the tetrasaccharide 133 with the method.

Although the disclosure is disclosed above with preferred examples, but they are not used for defining the disclosure. Any person skilled in the art can make various alternations and modifications without departing from the spirit and scope of the disclosure. Accordingly, the contents protected in the disclosure shall be based on what are defined in the claims.

What is claimed is:

1. A method for synthesizing an O-antigen oligosaccharide compound of *Helicobacter pylori* serotype O2, wherein the method comprises:
    synthesizing monosaccharide building blocks A, B, and C,
    synthesizing disaccharides by reacting the building blocks: (i) A and C to yield disaccharide D, and B and C to yield disaccharide E, or (ii) A and B to yield disaccharide I, wherein each disaccharide comprises one 1,2-α-cis-glycosidic bond, wherein reaction (i) is performed in a solvent at −78° C. with a drying agent present, and wherein reaction (ii) is performed in a solvent at −78° C. with a drying agent present and a Lewis acid present under inert gas, and
    synthesizing a tetrasaccharide F by reacting: (a) the disaccharide D with the disaccharide E, or (b) disaccharide I with itself, wherein each tetrasaccharide comprises one 1,3-α-cis-glycosidic bond, wherein reactions (a) and (b) are performed in the presence of thiophene in a mixed solvent of dichloromethane and diethylether, and wherein reaction (b) further comprises addition of a Lewis acid under inert gas;
wherein:
the monosaccharide building blocks A, B, and C are compounds represented by structural formulae II and III, respectively:

Formula II

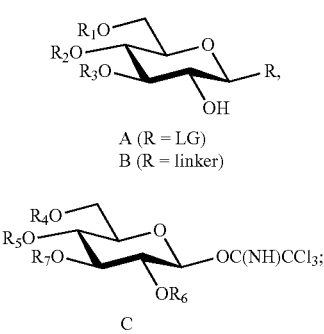

A (R = LG)
B (R = linker)

Formula III

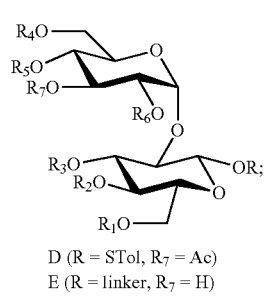

C the disaccharides D and E are compounds represented by structural formula V:

Formula V

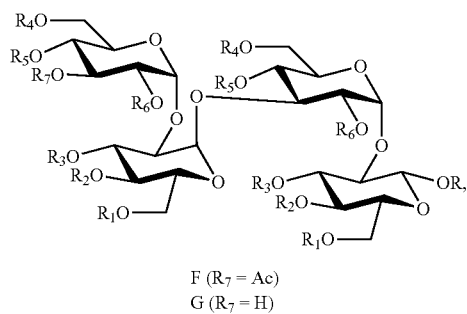

D (R = STol, $R_7$ = Ac)
E (R = linker, $R_7$ = H)

and
the tetrasaccharide F and a tetrasaccharide receptor G in a tetrasaccharide compound is represented by structural formula VI:

Formula VI

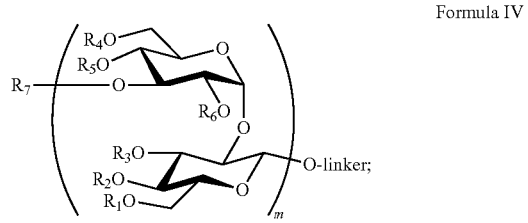

F ($R_7$ = Ac)
G ($R_7$ = H)

LG is a leaving group and comprises trichloroacetylimino or p-methylphenylthio;

linker comprises: —$(CH_2)_n$—N—$Y_1Y_2$, and wherein:
$Y_1$ is hydrogen or alkoxy,
$Y_2$ is hydrogen or alkoxycarbonyl,
n is 1 to 10, and
N is nitrogen;
$R_1$, $R_2$, $R_3$, $R_4$, $R_5$, and $R_6$ each are hydrogen or an ether group; and
$R_7$ is hydrogen or an acyl group.

2. The method according to claim 1, wherein a volume ratio of dichloromethane to diethylether in the mixed solvent is 1:(2.5-5).

3. The method according to claim 1, wherein a molar ratio of thiophene to the monosaccharide building blocks is (80-120):1.

4. The method according to claim 1,
wherein the synthesizing steps are repeated to produce polysaccharide compounds being compounds represented by formula IV:

Formula IV wherein:
m is the number of repeat units of a disaccharide fragment, and is 2 to 12;
linker
$R_1$, $R_2$, $R_3$, $R_4$, $R_5$, $R_6$, and
$R_7$ are as defined in claim 1.

5. The method of claim 1, further comprising crosslinking the linker to a protein thereby obtaining a glyco-protein conjugate.

* * * * *